US009253987B2

(12) United States Patent
Tennican et al.

(10) Patent No.: US 9,253,987 B2
(45) Date of Patent: *Feb. 9, 2016

(54) ANTIMICROBIAL AGENTS AND METHODS OF USE

(71) Applicant: Hyprotek, Inc., Spokane, WA (US)

(72) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 118 days.

This patent is subject to a terminal disclaimer.

(21) Appl. No.: 13/934,135

(22) Filed: Jul. 2, 2013

(65) Prior Publication Data

US 2013/0287861 A1 Oct. 31, 2013

Related U.S. Application Data

(63) Continuation of application No. 13/554,962, filed on Jul. 20, 2012, now Pat. No. 8,846,008, which is a continuation of application No. PCT/US2011/022150, filed on Jan. 21, 2011.

(60) Provisional application No. 61/412,375, filed on Nov. 10, 2010, provisional application No. 61/297,609, filed on Jan. 22, 2010.

(51) Int. Cl.
| | |
|---|---|
| *A61K 8/00* | (2006.01) |
| *A01N 59/00* | (2006.01) |
| *A61K 9/00* | (2006.01) |
| *A61K 9/08* | (2006.01) |
| *A61K 33/40* | (2006.01) |
| *A61K 47/10* | (2006.01) |
| *A61K 47/18* | (2006.01) |
| *A01N 31/02* | (2006.01) |
| *A61K 31/045* | (2006.01) |

(52) U.S. Cl.
CPC ............... *A01N 59/00* (2013.01); *A01N 31/02* (2013.01); *A61K 9/0014* (2013.01); *A61K 9/0063* (2013.01); *A61K 9/08* (2013.01); *A61K 31/045* (2013.01); *A61K 33/40* (2013.01); *A61K 47/10* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 3,607,760 A | 9/1971 | McIntyre | |
| 3,860,348 A | 1/1975 | Doyle | |
| 4,188,234 A | 2/1980 | Budnick | |
| 4,291,697 A | 9/1981 | Georgevich | |
| 4,440,207 A | 4/1984 | Genatempo et al. | |
| 4,564,010 A | 1/1986 | Coughlan et al. | |
| 4,811,847 A | 3/1989 | Reif et al. | |
| 4,813,210 A | 3/1989 | Masuda et al. | |
| 4,830,856 A | 5/1989 | Peppers | |
| 4,893,956 A | 1/1990 | Wojcik et al. | |
| 4,954,239 A | 9/1990 | Mueller | |
| 5,015,228 A | 5/1991 | Columbus et al. | |
| 5,041,264 A | 8/1991 | Williams | |
| 5,046,608 A | 9/1991 | Laipply | |
| 5,171,523 A | 12/1992 | Williams | |
| 5,438,984 A | 8/1995 | Schoendorfer | |
| 5,454,798 A | 10/1995 | Kubalak et al. | |
| 5,554,135 A | 9/1996 | Menyhay | |
| 5,556,375 A | 9/1996 | Ewall | |
| 5,569,207 A | 10/1996 | Gisselberg et al. | |
| 5,637,080 A | 6/1997 | Geng | |
| 5,713,842 A | 2/1998 | Kay | |
| 5,716,636 A | 2/1998 | Horstmann et al. | |
| 5,730,530 A | 3/1998 | Stoddard et al. | |
| 5,732,716 A | 3/1998 | Utecht | |
| 5,779,053 A | 7/1998 | Partika et al. | |
| 5,846,559 A | 12/1998 | Hopp | |
| 5,973,221 A | 10/1999 | Collyer et al. | |
| 6,063,029 A | 5/2000 | Saita et al. | |
| 6,071,541 A | 6/2000 | Murad | |
| 6,168,800 B1 | 1/2001 | Dobos et al. | |
| 6,455,066 B1 | 9/2002 | Fischer et al. | |
| 7,282,186 B2 | 10/2007 | Lake, Jr. et al. | |
| 7,478,962 B2 | 1/2009 | De Laforcade | |
| 7,482,021 B1 | 1/2009 | Tison et al. | |
| 7,762,044 B2 | 7/2010 | Clarke et al. | |
| 7,770,726 B2 | 8/2010 | Murray et al. | |
| 7,780,794 B2 | 8/2010 | Rogers et al. | |
| 7,799,010 B2 | 9/2010 | Tennican | |

(Continued)

FOREIGN PATENT DOCUMENTS

| | | |
|---|---|---|
| CN | 2546003 | 4/2003 |
| CN | 2705167 | 6/2005 |
| CN | 1711845 | 12/2005 |
| CN | 1813097 | 8/2006 |
| EP | 0262792 | 4/1988 |
| EP | 1687039 | 1/2009 |
| GB | 350384 | 6/1931 |
| JP | 6501857 | 3/1994 |
| JP | 07500751 | 1/1995 |
| JP | 10110268 | 4/1998 |

(Continued)

OTHER PUBLICATIONS

Chinese Office Action mailed Apr. 10, 2014 for Chinese patent application No. 201180006632.3, a counterpart foreign application of U.S. Appl. No. 13/554,962, 19 pages.

(Continued)

*Primary Examiner* — Snigdha Maewall
(74) *Attorney, Agent, or Firm* — Lee & Hayes, PLLC

(57) ABSTRACT

The present application relates to novel antimicrobial compositions and methods of using said antimicrobial compositions for inhibiting and treating microbial growth, microbial infections, inflammatory diseases, viral diseases, cardiovascular diseases, diabetes and/or conditions that may be regulated or associated with microbial infections, such as cancer.

12 Claims, No Drawings

(56) References Cited

U.S. PATENT DOCUMENTS

| | | | |
|---|---|---|---|
| 8,065,773 | B2 | 11/2011 | Vaillancourt et al. |
| 8,273,303 | B2 | 9/2012 | Ferlic et al. |
| 8,336,152 | B2 | 12/2012 | Vaillancourt et al. |
| 8,486,004 | B1 | 7/2013 | Propp |
| 8,496,625 | B2 | 7/2013 | Brugger et al. |
| 8,647,326 | B2 | 2/2014 | Solomon et al. |
| 8,777,504 | B2 | 7/2014 | Shaw et al. |
| 2003/0007939 | A1 | 1/2003 | Murad |
| 2003/0138479 | A1 | 7/2003 | Mizota et al. |
| 2004/0037789 | A1* | 2/2004 | Moneuze et al. ............... 424/49 |
| 2004/0110841 | A1 | 6/2004 | Kite et al. |
| 2005/0034731 | A1 | 2/2005 | Rousseau et al. |
| 2005/0084521 | A1 | 4/2005 | Hamada et al. |
| 2005/0129897 | A1 | 6/2005 | Zhou et al. |
| 2005/0265773 | A1 | 12/2005 | De Laforcade |
| 2006/0062834 | A1 | 3/2006 | Dixon |
| 2006/0129117 | A1 | 6/2006 | Malowaniec |
| 2006/0142684 | A1 | 6/2006 | Shanbrom |
| 2006/0151347 | A1 | 7/2006 | Grossman |
| 2006/0193816 | A1 | 8/2006 | Elfersy et al. |
| 2007/0179373 | A1 | 8/2007 | Pronovost |
| 2007/0246378 | A1 | 10/2007 | Cheaure et al. |
| 2007/0255193 | A1 | 11/2007 | Patel et al. |
| 2008/0057136 | A1 | 3/2008 | Polyakov et al. |
| 2008/0119801 | A1 | 5/2008 | Moore |
| 2008/0181950 | A1 | 7/2008 | Bates et al. |
| 2009/0010998 | A1 | 1/2009 | Marchitto et al. |
| 2009/0012496 | A1 | 1/2009 | Tennican |
| 2009/0028750 | A1 | 1/2009 | Ryan |
| 2009/0036541 | A1 | 2/2009 | Mardis |
| 2009/0324508 | A1 | 12/2009 | Bobbert |
| 2010/0003067 | A1 | 1/2010 | Shaw et al. |
| 2010/0030170 | A1 | 2/2010 | Keller et al. |
| 2010/0050351 | A1 | 3/2010 | Colantonio et al. |
| 2010/0078336 | A1 | 4/2010 | Reyhan et al. |
| 2010/0163435 | A1 | 7/2010 | Fischer et al. |
| 2010/0172794 | A1 | 7/2010 | Ferlic et al. |
| 2010/0260865 | A1 | 10/2010 | Kritzler |
| 2011/0052664 | A1 | 3/2011 | Tennican et al. |
| 2011/0184382 | A1 | 7/2011 | Cady |
| 2011/0265834 | A1 | 11/2011 | Tennican |
| 2011/0295207 | A1 | 12/2011 | Brugger et al. |
| 2012/0288571 | A1 | 11/2012 | Tennican et al. |
| 2013/0138085 | A1 | 5/2013 | Tennican |
| 2013/0287860 | A1 | 10/2013 | Tennican et al. |
| 2014/0243725 | A1 | 8/2014 | Tennican et al. |

FOREIGN PATENT DOCUMENTS

| | | |
|---|---|---|
| JP | 2001525688 | 12/2001 |
| JP | 2004049540 | 2/2004 |
| JP | 2005511147 | 4/2005 |
| JP | 2005350571 A | 12/2005 |
| JP | 2006503647 | 2/2006 |
| JP | 2006526664 | 11/2006 |
| JP | 2007505093 | 3/2007 |
| JP | 2007536261 | 12/2007 |
| JP | 2008503485 | 2/2008 |
| JP | 2009519312 | 5/2009 |
| JP | 2013503713 | 2/2013 |
| WO | WO8503275 | 8/1985 |
| WO | WO9204923 | 4/1992 |
| WO | WO9308777 | 5/1993 |
| WO | WO0156540 | 8/2001 |
| WO | WO2004091675 | 10/2004 |
| WO | WO2004108091 | 12/2004 |
| WO | WO2005003436 | 1/2005 |
| WO | WO2005025486 | 3/2005 |
| WO | WO2005062896 | 7/2005 |
| WO | WO2005089341 | 9/2005 |
| WO | WO2006009853 | 1/2006 |
| WO | WO2006/089139 A2 | 8/2006 |
| WO | WO2007068938 | 6/2007 |
| WO | WO2007137056 | 11/2007 |
| WO | WO2008003779 | 1/2008 |
| WO | WO2008009925 | 1/2008 |
| WO | WO2009076718 | 6/2009 |
| WO | WO2011019132 | 7/2011 |
| WO | WO2011163124 | 12/2011 |
| WO | WO2013082187 | 6/2013 |

OTHER PUBLICATIONS

Chinese Office Action mailed Apr. 22, 2014 for Chinese patent application No. 201080047665.8, a counterpart foreign application of U.S. Appl. No. 12/874,188, 17 pages.

European Search Report mailed Apr. 23, 2014 for European patent application No. , 11 pages.

Hospenthal et al., "Guidelines for the Prevention of Infections After Combat-Related Injuries", Journal of Trauma Injury, Infection, and Critical Care, vol. 64, No. 3, Mar. 2008, pp. S211-S220.

McGee et al., "Preventing Complications of Central Venous Catheterization", The New England Journal of Medicine, vol. 348, No. 12, Mar. 20, 2003, pp. 1123-1133.

Final Office Action for U.S. Appl. No. 12/874,188, mailed Dec. 19, 2012, Patrick O. Tennican et al., "Antimicrobial Medical Dressings and Protecting Wounds and Catheter Sites", 6 pages.

Non-Final Office Action for US Patent Application mailed on Feb. 15, 2013, Patrick O. Tennican et al., "Antimicrobial Agents and Methods of Use", 12 pages.

Non-Final Office Action for U.S. Appl. No. 12/874,188, mailed Jun. 29, 2012, Patrick O. Tennican et al., "Antimicrobial Medical Dressings and Protecting Wounds and Catheter Sites", 6 pages.

PCT Search Report mailed May 20, 2011 for PCT Appliction No. PCT/US10/47756.

PCT Search Report mailed Aug. 1, 2011 for PCT application No. PCT/US11/22150.

Singhal et al., "Wound Infection", eMedicine from WebMD <<http://www.emedicine,medscape.com>>, Updated Sep. 15, 2009, 32 pages.

"VERSENE Acid—Solubility", The Dow Chemical Company, Sep. 15, 2010, pp. 1-3.

"VERSENE NA Disodium EDTA Chelating Agent", The Dow Chemical Company, Oct. 2009, pp. 1-2.

Australian Office Action mailed Mar. 13, 2014 for Australian patent application No. 2011207398, a counterpart foreign application of U.S. Appl. No. 13/554,962, 3 pages.

Non-Final Office Action for U.S. Appl. No. 12/874,188, mailed Feb. 7, 2014, Patrick O. Tennican et al., "Antimicrobial Medical Dressings and Protecting Wounds and Catheter Sites", 6 pages.

Office Action for U.S. Appl. No. 13/924,410, mailed on Mar. 28, 2014, Patrick O. Tennican, "Antimicrobial Agents and Methods of Use", 18 pages.

Chinese Office Action mailed Aug. 12, 2013 for Chinese patent application No. 201080047665.8, a counterpart foreign application of U.S. Appl. No. 12/874,188, 13 pages.

Office action for U.S. Appl. No. 12/874,188, mailed on Sep. 10, 2013, Tennican et al., "Antimicrobial Medical Dressings and Protecting Wounds and Catheter Sites", 6 pages.

Chinese Office Action mailed Oct. 23, 2014 for Chinese patent application No. 201080047665.8, a counterpart foreign application of U.S. Pat. No. 8,778,387, 13 pages.

Chinese Office Action mailed Sep. 25, 2014 for Chinese patent application No. 201180006632.3, a counterpart foreign application of U.S. Appl. No. 13/554,962, 19 pages.

Office action for U.S. Appl. No. 13/757,318, mailed on Aug. 26, 2014, Tennican, "Antiseptic Applicators and Packaging Techniques", 9 pages.

Office action for U.S. Appl. No. 13/757,423, mailed on Sep. 4, 2014, Tennican, "Adhesive Patch with Antimicrobial Composition", 13 pages.

PCT Search Report mailed May 15, 2013 for PCT application No. PCT/US13/24635, 10 pages.

PCT Search Report mailed May 13, 2013 for PCT application No. PCT/US13/24644, 10 pages.

PCT Search Report mailed May 15, 2013 for PCT application No. PCT/US13/24651, 12 pages.

(56) References Cited

OTHER PUBLICATIONS

PCT Search report mailed May 31, 2013 for PCT application No. PCT/US13/24649, 14 pages.
Chinese Office Action mailed Oct. 17, 2013 for Chinese patent application No. 201180006632.3, a counterpart foreign application of U.S. Appl. No. 13/554,962, 13 page.
Australian Office Action mailed Nov. 4, 2013 for Australian patent application No. 2010289415, a counterpart foreign application of U.S. Appl. No. 12/874,188, 3 pages.
Final Office Action for U.S. Appl. No. 13/554,962, mailed on Dec. 5, 2013, Patrick O. Tennican, "Antimicrobial Agents and Methods of Use", 14 pages.
Office Action for U.S. Appl. No. 13/924,410, mailed on Nov. 22, 2013, Patrick O. Tennican, "Antimicrobial Agents and Methods of Use", 15 pages.
European Office Action mailed Sep. 12, 2014 for European patent application No. 11701925.7, a counterpart foreign application of U.S. Pat. No. 8,846,008, 5 pages.
Japanese Office Action mailed Aug. 19, 2014 for Japanese patent application No. 2012-528071, a counterpart foreign application of U.S. Pat. No. 8,778,387, 10 pages.
Japanese Patent No. JP6501857, which corresponds to International Patent Publication No. WO92/04923.
Office action for U.S. Appl. No. 14/271,365, mailed on Sep. 11, 2014, Tennican et al., "Antimicrobial Medical Dressings and Protecting Wounds and Catheter Sites", 7 pages.
Mexican Office Action mailed Jul. 2, 2014 for Mexican patent application No. MX/A/2012/008482, a counterpart foreign application of U.S. Appl. No. 13/554,962, 2 pages.
Mexican Office Action mailed May 26, 2014 for Mexican patent application No. MX/a/2012/002746, a counterpart foreign application of U.S. Pat. No. 8,778,387, 4 pages.
Chinese Office Action mailed Apr. 8, 2015 for Chinese patent application No. 201180006632.3, a counterpart foreign application of U.S. Pat. No. 8,846,008, 19 pages.
Chinese Office Action mailed Apr. 9, 2015 for Chinese patent application No. 201080047665.8, a counterpart foreign application of U.S. Pat. No. 8,778,387, 8 pages.
Japanese Office Action mailed Dec. 24, 2014 for Japanese patent application No. 2012-550177, a counterpart foreign application of U.S. Pat. No. 8,846,008, 4 pages.
Japanese Office Action mailed Apr. 14, 2015 for Japanese patent application No. 2012-528071, a counterpart foreign application of U.S. Pat. No. 8,778,387, 9 pages.
Mexican Office Action mailed Jan. 13, 2015 for Mexican patent application No. MX/a/2012/002746, a counterpart foreign application of U.S. Pat. No. 8,778,387, 2 pages.
Office Action for U.S. Appl. No. 14/271,365, mailed on Jan. 23, 2015, Patrick O. Tennican, "Antimicrobial Medical Dressings and Protecting Wounds and Catheter Sites", 8 pages.
Office Action for U.S. Appl. No. 13/757,465, mailed on Feb. 9, 2015, Patrick O. Tennican, "Combined Cap Applicators", 14 pages.
Non-Final Office Action for U.S. Appl. No. 13/757,423, mailed on Apr. 10, 2015, Patrick O. Tennican, "Adhesive Patch with Antimicrobial Composition", 13 pages.
Final Office Action for U.S. Appl. No. 13/757,465, mailed on May 28, 2015, Patrick O. Tennican, "Combined Cap Applicators", 15 pages.
Final Office Action for U.S. Appl. No. 14/271,365, mailed on Jun. 1, 2015, Patrick O. Tennican, "Antimicrobial Medical Dressings and Protecting Wounds and Catheter Sites", 10 pages.
Russian Office Action mailed Jan. 23, 2015 for Russian patent applcation No. 2012136147, a counterpart foreign application of US patent application No. , pages.
Office Action for U.S. Appl. No. 13/757,381, mailed on Jul. 1, 2015, Patrick O. Tennican, "Portable Medical Device Protectors", 9 pages.
Extended European Search Report mailed Mo Sep. 10, 2015 for European Patent Application No. 13747071.2, 8 pages.
Extended European Search Report mailed Sep. 11, 2015 for European Patent Application 13746209.9, 6 pages.
Extended European Search Report mailed Sep. 17, 2015 for European patent application No. 13746984.7, 7 pages.
Japanese Office Action mailed Aug. 11, 2015 for Japanese patent application No. 2012-550177, a counterpart foreign application of U.S. Pat. No. 8,846,008, 4 pages.
Office Action for U.S. Appl. No. 14/271,365, mailed on Oct. 2, 2015, Patrick O. Tennican, "Antimicrobial Medical Dressings and Protecting Wounds and Catheter Sites", 9 pages.
Extended European Search Report mailed Sep. 18, 2015 for European Patent Application No. 13746515.9, 7 pages.
Final Office Action for U.S. Appl. No. 13/757,423, mailed on Oct. 27, 2015, Patrick O. Tennican, "Adhesive Patch with Antimicrobial Composition", 12 pages.
Office action for U.S. Appl. No. 13/757,381, mailed on Nov. 25, 2015, Tennican et al., "Portable Medical Device Protectors", 7 pages.
Australian Office Action mailed Nov. 16, 2015 for Australian patent application No. 2013217602, a counterpart foreign application of U.S. Pat. No. 9,039,967, 3 pages.
Chinese Office Action mailed Nov. 4, 2015 for Chinese patent application No. 201380008084.7, a counterpart foreign application of U.S. Pat. No. 9,192,443, 22 pages.

\* cited by examiner

ANTIMICROBIAL AGENTS AND METHODS OF USE

CROSS REFERENCE TO RELATED PATENT APPLICATIONS

This application is a continuation of U.S. patent application Ser. No. 13/554,962 filed Jul. 20, 2012, entitled "Antimicrobial Agents and Methods of Use," which claims priority to, and is a continuation of, PCT International Application No. PCT/US11/22150 filed Jan. 21, 2011 which claims priority to U.S. Provisional Patent Application No. 61/412,375 filed on Nov. 10, 2010, entitled "Antimicrobial Agents and Methods of Use," and to U.S. Provisional Patent Application No. 61/297,609 filed on Jan. 22, 2010, entitled "Antimicrobial and Immunomodulatory Agents and Methods of Use," of which are hereby incorporated by reference in their entirety.

TECHNICAL FIELD

The present application relates to novel antimicrobial compositions and methods of using said antimicrobial compositions for inhibiting and treating microbial growth, microbial infections, inflammatory diseases, viral diseases, cardiovascular diseases, diabetes and/or conditions that may be regulated or associated with microbial infections, such as cancer.

BACKGROUND

The formation of biofilms on the surface of medical devices is a serious and increasing problem for the medical community. Biofilms form on many types of surfaces, composed of a wide variety of materials, including catheters and ports, metal surfaces such as implanted prosthetic devices, live tissue such as deep wound trauma areas, and oral tissues such as teeth, gum tissue and bone. A number of types of organisms can originate biofilms including bacteria and fungi. Further, while some biofilms can be occupied by a single species, more commonly biofilms consist of an entire community of a variety of organisms. In some cases, even viruses can participate in the pathology generated by the biofilm community by way of bacteriophages. Both gram-negative and gram-positive bacterial organisms as well as fungi can produce biofilms.

While occupying a biofilm, many organisms, especially pathogens, exhibit a changed profile of sensitivities or resistances to antibiotics. This, coupled with the physico-chemical protections provided by the biofilm, make treating patients with biofilm infections very difficult. The problem is increasingly difficult as more organisms become antibiotic resistant, even when means can be found to deliver an effective dose of an antibiotic to the biofilm occupants.

An additional problem arises when trying to design an antimicrobial treatment to destroy a biofilm infection utilizing either small molecule agents or antibiotic agents that are strongly effective against planktonic forms of biofilm organisms. The problem lies in the inability of the antimicrobial agents, such as antibiotics, to penetrate the biofilm due in part to the biofilm acting to protect the embedded microorganisms by preventing or reducing the antibiotic diffusion, thus only reaching the target organisms in lowered concentration. One means by which this form of barrier could operate is to react with the incoming antimicrobial agent at or near the surface, converting it into a different and potentially less lethal form. Another mechanism is physiology-based, positing that the biofilm-bound organisms are essentially undergoing modified metabolic process, relative to the planktonic counterparts, the modification of which reduces their susceptibility to the antibiotic agent. Thus, the design of effective antimicrobial agents has presented many challenges.

During a microbial infection, various cellular stress responses are also triggered, leading to tissue inflammation and immune cell activation. These immune events, in turn, may promote the development of and/or sustain pathways that underlie downstream disorders such as cancer. However, molecular events linking these processes are not well understood, hindering efforts to uncover effective immune modulators that may be useful for the treatment of downstream immune-associated conditions.

BRIEF SUMMARY

The present application relates to the discovery of a novel combination of ingredients that collectively are effective as an antimicrobial agent. Accordingly, the present application describes novel compositions and methods of using the antimicrobial agent for inhibiting and treating microbial growth, microbial infections as well as inflammatory diseases, viral diseases, cardiovascular diseases, diabetes and conditions that may be regulated or associated with microbial infections, such as cancer or pre-cancerous conditions.

In one embodiment, the present application provides an antimicrobial agent comprising (a) water; (b) a low molecular weight alcohol; (c) a peroxide or peroxide-generating agent; and (d) a chelating agent.

In some embodiments, the alcohol in the antimicrobial agent comprises ethanol. In some embodiments, the alcohol is present in the antimicrobial agent at a concentration of from about 1% to about 95% by volume. In other embodiments, the alcohol is present from about 20% to about 60% by volume. In alternative embodiments, the alcohol is present at about 50% by volume.

In some embodiments, the chelating agent in the antimicrobial agent comprises ethylenediamine tetraacetic acid (EDTA) and its acids and salts thereof. In some embodiments, the EDTA is present at a concentration of from about 5 mg/mL to about 50 mg/mL. In other embodiments, the EDTA is present at a concentration of about 10 mg/mL.

In some embodiments, the peroxide or peroxide-generating agent in the antimicrobial agent comprises hydrogen peroxide ($H_2O_2$). In some embodiments, the $H_2O_2$ is present at a concentration of from about 0.05% to about 40% by volume. In other embodiments, the $H_2O_2$ is present at a concentration of from about 0.05% to about 10% by volume. In alternative embodiments, the $H_2O_2$ is present at a concentration of about 1.5% by volume.

In some embodiments, the antimicrobial agent further comprises a viscosity-increasing agent. In some embodiments, the viscosity-increasing agent comprises hydroxypropyl methylcellulose (HPMC).

In some embodiments, the antimicrobial agent is useful in reducing or inhibiting microbial growth, microbial infections, inflammatory diseases, viral diseases, cardiovascular diseases, diabetes or conditions resulting from or associated with microbial growth or infection. In some embodiments, the antimicrobial agent is useful in treating microbial growth, microbial infections, inflammatory diseases, viral diseases, cardiovascular diseases, diabetes or conditions resulting from or associated with microbial growth or infection.

In another embodiment, the present application provides a method of inhibiting or reducing microbial growth, comprising administering to a subject a therapeutically effective amount of an antimicrobial agent comprising: (a) water; (b) a low molecular weight alcohol; (c) a peroxide or peroxide-generating agent; and (d) a chelating agent. In another embodiment, the present application relates to a method of treating microbial growth, comprising administering to a subject a therapeutically effective amount of an antimicrobial agent comprising: (a) water; (b) a low molecular weight alcohol; (c) a peroxide or peroxide-generating agent; and (d) a chelating agent.

In another embodiment, the present application relates to a method of inhibiting or reducing a microbial infection, comprising administering to a subject a therapeutically effective amount of an antimicrobial agent comprising: (a) water; (b) a low molecular weight alcohol; (c) a peroxide or peroxide-generating agent; and (d) a chelating agent. In another embodiment, the present application relates to a method of treating a microbial infection, comprising administering to a subject a therapeutically effective amount of an antimicrobial agent comprising: (a) water; (b) a low molecular weight alcohol; (c) a peroxide or peroxide-generating agent; and (d) a chelating agent.

In some embodiments, the microbial growth or microbial infection is due to a microorganism selected from the group consisting of a bacterium, a fungus, a protozoa and a virus.

In some embodiments, the methods are for treating microbial growth or microbial infection associated with a medical device.

In another embodiment, the present application relates to a method of inhibiting or reducing an inflammatory condition or disease comprising administering to a subject a therapeutically effective amount of an antimicrobial agent comprising: (a) water; (b) a low molecular weight alcohol; (c) a peroxide or peroxide-generating agent; and (d) a chelating agent. In another embodiment, the present application relates to a method of treating an inflammatory condition or disease comprising administering to a subject a therapeutically effective amount of an antimicrobial agent comprising: (a) water; (b) a low molecular weight alcohol; (c) a peroxide or peroxide-generating agent; and (d) a chelating agent.

In another embodiment, the present application relates to a method of inhibiting or reducing a viral condition or disease comprising administering to a subject a therapeutically effective amount of an antimicrobial agent comprising: (a) water; (b) a low molecular weight alcohol; (c) a peroxide or peroxide-generating agent; and (d) a chelating agent. In another embodiment, the present application relates to a method of treating a viral condition or disease comprising administering to a subject a therapeutically effective amount of an antimicrobial agent comprising: (a) water; (b) a low molecular weight alcohol; (c) a peroxide or peroxide-generating agent; and (d) a chelating agent.

In some embodiments, the methods for treating inflammatory or viral conditions or diseases are associated with microbial growth or microbial infection. In some embodiments, the microbial growth or microbial infection is associated with a medical device.

In some embodiments, the methods for treating inflammatory conditions are associated with cardiovascular diseases, diabetes and cancer or pre-cancerous conditions. In other embodiments, the methods for treating viral conditions are associated with cardiovascular diseases, diabetes and cancer or pre-cancerous conditions.

In another embodiment, the present application relates to a method of inhibiting or reducing a condition or disease resulting from or associated with microbial growth or infection comprising administering to a subject a therapeutically effective amount of an antimicrobial agent comprising: (a) water; (b) a low molecular weight alcohol; (c) a peroxide or peroxide-generating agent; and (d) a chelating agent. In another embodiment, the present application relates to a method of treating a condition or disease resulting from or associated with microbial growth or infection comprising administering to a subject a therapeutically effective amount of an antimicrobial agent comprising: (a) water; (b) a low molecular weight alcohol; (c) a peroxide or peroxide-generating agent; and (d) a chelating agent.

In some embodiments, the condition or disease resulting from or associated with microbial growth or infection is selected from the group consisting of cancer or pre-cancerous conditions, inflammatory disease and viral disease. In some embodiments, the condition is cancer or pre-cancerous conditions.

In another embodiment, the present application relates to a method of inhibiting or reducing an immune response comprising administering to a subject a therapeutically effective amount of an antimicrobial agent comprising: (a) water; (b) a low molecular weight alcohol; (c) a peroxide or peroxide-generating agent; and (d) a chelating agent.

In some embodiments, the methods of inhibiting or reducing an immune response comprises administering the antimicrobial agent at an amount effective in inhibiting local or systemic toxicity. In some embodiments, the antimicrobial agent is at an amount effective in inhibiting cytokine or chemokine levels or activity and/or cytokine or chemokine receptor levels or activity. In some embodiments, the inhibition of cytokine or chemokine levels or activity is the result of chemical inhibition or modification of the cytokine or chemokine and/or its receptor.

In some embodiments, the immune response is associated with cancer or pre-cancerous conditions, inflammatory disease, viral disease, microbial infection, cardiovascular disease or diabetes. In some embodiments, the immune response is associated with cancer or pre-cancerous conditions. In some embodiments, the microbial infection is due to a microorganism selected from the group consisting of a bacterium, a fungus, a protozoa and a virus.

In another embodiment, the present application relates to a method of inhibiting or reducing biofilm formation, comprising: identifying a site; and applying an antimicrobial agent to the site, the antimicrobial agent comprising: (a) water; (b) a low molecular weight alcohol; (c) a peroxide or peroxide-generating agent; and (d) a chelating agent.

In some embodiments, the biofilm formation is the result of microbial growth or microbial infection. In some embodiments, the microbial growth or microbial infection is due to a microorganism selected from the group consisting of a bacterium, a fungus, a protozoa and a virus.

In some embodiments, the subject is human.

In some embodiments, the antimicrobial agent is administered by topical application, intravenous injection, intraperitoneal injection or implantation, intramuscular injection or implantation, intralesional injection (within a tumor), subcutaneous injection or implantation, intradermal injection, suppositories, pessaries, enteric application, or nasal route. In some embodiments, the agent is administered by topical application.

In some embodiments, the antimicrobial agent is administered to a site selected from the group consisting of a wound site, a catheter site, a surgical site, an injection site, a catheter, a catheter lumen, a thermal burn site, a chemical burn site, a radiation burn site, a skin lesion, oral sites, bony sites, anal sites, vaginal sites, cervical sites, vulvar sites, penile sites, ulcerated skin sites, acne sites, actinic keratosis sites, inflamed sites, irritated sites, gastric sites, gastrointestinal sites, esophageal sites, esophagogastrointestinal sites, intestinal sites, cardiac sites, vascular sites, nasal sites, nasopharyngeal sites, and aural sites.

This Brief Summary is provided to introduce simplified concepts related to antimicrobial compositions and methods of using said antimicrobial compositions, which are further described below in the Detailed Description. This summary is not intended to identify essential features of the claimed subject matter, nor should it be used to limit the scope of the claims.

DETAILED DESCRIPTION OF THE APPLICATION

Unless otherwise defined, all technical terms used herein have the same meaning as commonly understood by one of ordinary skill in the art to which this application belongs.

As used herein, the terms "subject," "patient" and "individual" are used interchangeably herein, and mean a mammalian (e.g., human) subject to be treated and/or to obtain a biological sample from.

As used herein, the term "sample" is used herein in its broadest sense. For example, a sample including polynucleotides, peptides, antibodies and the like may include a bodily fluid, a soluble fraction of a cell preparation or media in which cells were grown, genomic DNA, RNA or cDNA, a cell, a tissue, skin, hair and the like. Examples of samples include biopsy specimens, serum, blood, urine, plasma and saliva.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used as described herein.

As used herein, the term "therapeutically effective amount" means an amount of a composition as described herein effective to yield the desired therapeutic response.

The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, the term "treatment" is defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease. For example, "treatment" of a patient in whom no symptoms or clinically relevant manifestations of a disease or disorder have been identified is preventive or prophylactic therapy, whereas clinical, curative, or palliative "treatment" of a patient in whom symptoms or clinically relevant manifestations of a disease or disorder have been identified generally does not constitute preventive or prophylactic therapy.

Compositions and methods similar or equivalent to those described herein can be used in the practice or testing of the present application. Suitable compositions and methods are described below.

There is a need for identifying improved antimicrobial agents with improved activity (and in some cases with reduced toxicity), for optimal therapeutic use, and for developing therapeutically effective clinical regimens for these antimicrobial agents. Furthermore, there is a need for formulations that are useful in a variety of related clinical indications. The present application meets such needs, and further provides other related advantages.

The present application is based on a novel combination of ingredients intended to act as an antimicrobial agent in medical applications. The antimicrobial agent of the present application comprises at least three ingredients, and is designed such that all ingredients in the antimicrobial agent are compatible with being placed in small quantities within a human or animal patient's body with no long term undesirable effects. The individual ingredients within the antimicrobial agent of the present application are known to be safe for application onto or into the human or animal body in at least low levels. The present application relates to a novel combination of the individual ingredients which provide a significant level of antimicrobial, antibacterial, antifungal, anti-inflammatory or antiviral action, or antibiofilm or immunomodulatory action or some combination of these properties.

Biofilm Formation

The formation of biofilms on many types of surfaces is a serious and increasingly unmet medical problem. It can form on many surfaces including catheters and ports, metal surfaces such as implanted prosthetic devices, live tissue such as deep wound trauma areas and oral tissues such as teeth, gum tissue and bone, to name but a few.

The development of antibiotic resistance by many of the microorganisms occupying biofilms complicates the design of effective therapeutics. In addition, penetration into the biofilm by an agent poses a significant hurdle. Two scenarios have been postulated to attempt to explain the mechanisms underlying the penetration into biofilms and the bacterial resistance that results. First is a transport-based explanation, suggesting that the biofilm is acting to protect the embedded microorganisms by preventing or reducing the antibiotic diffusion, thus only reaching the target organisms in reduced concentration. One means by which this form of barrier could operate is to react with the incoming antimicrobial agent at or near the surface, converting it into a different and potentially less lethal form. A second explanation is physiology-based, positing that the biofilm-bound organisms are essentially undergoing modified metabolic process, relative to the planktonic counterparts, the modification of which reduces their susceptibility to the antibiotic agents.

Quorum Sensing

Among the most significant advances in understanding of biofilms has been the discovery of quorum sensing (QS) as the means by which biofilm-forming bacteria, communicate their own presence and initiate the process of biofilm formation when their numbers reach a certain threshold value. The search for the molecular-level communication "trigger" resulted in the identification of the family of acyl homoserine lactones (AHL's) as the primary quorum sensing communication molecule in gram-negative bacteria. In gram-positive bacteria, quorum sensing involves a cascade of at least three steps, but the predominant one, at least in some species is AHL. It is now understood that in both gram-negative and gram-positive bacteria, detection of the QS signal is via gene expression. When AHL is able to occupy the binding site of the sensing molecule, it begins the cascade of reactions which result in the production of the exopolysaccharide "slime" of the biofilm.

A similar family of molecules provides a quorum sensing function in gram-positive bacteria, although the studied cases are fewer. In at least some cases, gram-positive bacteria use a three-step quorum sensing pathway, but the pathway involving AHL is still the primary feature. In at least one case, Vibrio harveyi, a marine organism, the QS system is well studied, and involves three parallel systems. Even in that more complex case, though the AHL system is primary. In that specific case, the AHL variant is N-(3-hydroxybutanoyl) homoserine lactone.

The AHL's all posses the lactone ring and the 3-position N-atom. Variations in the structure occur primarily in the N-bound chain, varying size, shape, chain length, saturation, and the presence or absence of hetero-atoms. Variation between species occurs. Among these variations are degrees of saturations in the N-bound side chain. A few cases are known wherein the side chain is cyclic. There is evidence that indicate that AHL's bind to the active site of a trigger molecule which in turn initiates the production of exopolysaccharide (EPS), the major building block of biofilms. Included in the evidence is that a series of 3-substituted furanones have been shown to be strong antagonists of the AHL binding. These furanones are structurally similar to the AHL's, of course, some occur naturally and some are synthetic, some are hetero-atom substituted for example with Br and are 3-substituted with side-chains of approximately similar structure. Often, within the furanone ring structures are unsaturations (i.e., C=C bonds), which are not directly similar to the lactone ring of AHL. These ring-unsaturations do not prevent the AHL antagonism of the furanone. Because the furanone's key structural component is its ring rather than its side chain, changes in side-chain do not cause large changes in the antagonism, while changes, such as for example halogen substitution in the ring's substituents do.

A second indicative feature of the furanone behavior is that the furanone is generally unable to completely block the AHL binding. This is generally considered to indicate a competitive binding between native AHL and the receptor, or between a similar structure of the (non-native) furanone and the receptor. If that be the case, the competitive binding is most likely to also be reversible although to our knowledge that has not been established.

Assuming that the binding is reversible in both cases, these equilibria, shown in Eqn. 1 and Eqn. 2 would apply: We let [LuX-1 initiator]=1

LuX 1 initiator+AHL⇔LuX 1-AHL  Eqn. 1:

$K_{AHL}$=[LuX 1-AHL]/[AHL]

Lux 1 inducer+Fur⇔LuX 1-Fur  Eqn 2:

$K_{Fur}$=[LuX 1-Fur]/[Fur] where Kfur~1

The assignment of the K-value of the Kfur is approximate, based on values for similar reactions. The design of the antimicrobial agent of the present application took into consideration the desired reaction between alcohol (i.e., particularly ethanol (EtOH)) and AHL and which would be effective in the destruction of biofilms. The antimicrobial agent of the present application comprises an advantageous mixture of EtOH, hydrogen peroxide ($H_2O_2$), and a chelator, specifically ethylenediamine tetraacetic acid (EDTA). Thus, the antimicrobial agent of the present application has at least two features known to be anti-biofilm, simply based on its composition.

EDTA has been reported to disrupt some biofilms, and EtOH is toxic to a variety of biofilm bacteria, including those inhabiting biofilms, as well as those that are planktonic. In order to enhance the spectrum of cases in which pathogenic organisms are destroyed, the antimicrobial agent of the present application will also inhibit or prevent biofilm formation. This strategy will improve the killing spectrum of our antimicrobial agent by inhibiting biofilm formation, thus keeping a greater percentage of bacteria in the planktonic state, i.e., keeping them in the state in which they are more vulnerable to killing by antibacterial or antibiotic agents. One means by which this goal might be achieved is to interrupt the QS system which, in turn, prevents the transition from the planktonic to the biofilm state.

Our approach to AHL disruption is different from previous work. Rather than trying to develop an enzyme blocking substance that specifically occupies the AHL-binding site, we opted for a change in the chemical structure of AHL itself. If the content of AHL is never allowed to reach the critical level required for QS, all the bacteria will stay unprotected and vegetative.

There are several well-known reactions which might allow the non-oxidative disruption of the AHL molecule at mild temperatures, near-neutral pH and in an alcoholic aqueous solution such as the antimicrobial agent of the present application.

Option 1: Ring-opening hydrolysis at the lactone function:

AHL+$H_2O$<=>HO—($CH_2$)$_2$—CH—(CONH—R)—COOH

Option 2: Ring opening ethanolysis (i.e., transesterification) at the lactone function:

AHL+EtOH<=>HO—($CH_2$)$_2$—CH—(CONH—R)—COOEt

Option 3: Hydrolysis of the amide function in the side chain by water:

AHL+$H_2O$<=>3-amino tetrahydrofuran-2-one+HOOC—R (generally a fatty acid.)

All these reactions are equilibria, whose specific equilibrium constants are not readily found. However, several chemical principles can be used to estimate their reaction parameters to determine if they provide the needed entry into biofilm prevention or inhibition. First, even if the equilibrium constant of the hydrolysis is unfavorably small, e.g., if the AHL structure is favored by the thermodynamics or kinetics of the ring-opening hydrolysis or ethanolysis, reasonable amounts of reaction might occur because of the large difference in concentrations. AHL's are known to be active in nanomolar (nM) concentrations. On the other hand, a typical antimicrobial agent of the present application might contain, for example, 20-60% EtOH in water by volume. The density of these solutions is near 1.0-1.2 g/mL. This suggests that a 60% EtOH solution would contain about 500-600 g/L of EtOH, i.e., about 11 M in EtOH and about 28-30 M in water. These levels exceed the AHL concentration by factors of $10^9$. Thus, even if the equilibrium constant is very unfavorable, small but likely sufficient amounts of hydrolysis/ethanolysis would be expected at equilibrium.

However, the second phase reaction, namely oxidative consumption of the hydrolysis/ethanolysis product can occur, since $H_2O_2$ is present in the antimicrobial agent of the present invention at levels typically around 3-6% (around 1.5 M-3.0 M). Peroxide reactions are often driven by fast kinetics, generally based on reactive free radicals, and/or by the physical escape of a reaction product, for example by emission of a gas. Thus, in such a situation, the equilibrium between unmodified AHL and either water or ethanol would be expected to shift towards the hydrolyzed or ethanolysed product as its equilibrium partner is rapidly converted to another species. AHL is thus removed from the solution or its concentration is so lowered as to hold it to levels below the critical QS threshold. Therefore, QS will be interrupted, even with high inoculums of bacteria present.

Antimicrobial Agents of the Present Application

The antimicrobial agents of the present application comprise an alcohol, a peroxide or peroxide-generating agent and a chelating agent, with the remaining balance being made up of water. The unique design feature of the antimicrobial agent of the present application and the synergistic effects derived from the combination of the individual components provide a spectrum of effects that avoid the pitfalls of single-component treatments.

The antimicrobial agents of the present application comprise an alcohol, preferably a low molecular weight alcohol. It can be present at a concentration of from about 1% to about 95% by volume, preferably from about 20% to about 60% by volume, and more preferably at about 50% by volume. Exemplary alcohols that are contemplated within the present application include but are not limited to ethanol, isopropyl alcohol, n-propyl alcohol, butanol, pentanol, phenol and phenol derivatives, furanol and furanol derivatives, diols, triols, polyols, including chain, ring and aromatics, and the like. An antimicrobial agent comprising ethanol, and preferably about 50% by volume, is preferred.

The antimicrobial agents of the present application also comprise a peroxide or peroxide generating agent. It is present at a concentration of from about 0.05% to about 40% by volume, preferably from about 0.05% to about 10% by volume, and more preferably at about 1.5% by volume. Exemplary peroxide or peroxide-generating agents that are contemplated within the present application include but are not limited to hydrogen peroxide $H_2O_2$, carbamide peroxide (i.e., urea peroxide), peroxy acids such as peroxyacetic acid, peroxybenzoic acid, acetic anhydride, and the like. In some cases, free-hydroxyl or free-radical generating substances could be present or a substitute for hydrogen peroxide. Exemplary free-radical generating substances that are contemplated within the present application include but are not limited to acetone peroxide, t-butyl peroxide, di-t-butyl diazine $((t-Bu)_2 N_2)$, and the like. Other free-radical generating materials include those which generate free radicals on exposure to, for example, UV light. An antimicrobial agent comprising $H_2O_2$, and preferably about 1.5% by volume is preferred.

The antimicrobial agents of the present application further comprise one or more compounds that are chelating agents (chelators). They are present in the antimicrobial agents of the present application in the form which results when the pH of the solution is adjusted to the desired level for a particular application. Exemplary chelating agents that are contemplated within the present application include but are not limited to ethylenediamine tetraacetic acid (EDTA), citrate, and their salts, other substituted compounds, such as salicylic acid or salicylate esters, and the like. An antimicrobial agent comprising EDTA, and preferably at a concentration of from about 5 mg/mL to about 50 mg/mL, more preferable at a concentration of about 10 mg/mL is preferred.

While not wishing to be limited by any particular theory, chelators are primarily known to act to form strong bonds to a wide variety of inorganic or organic ions, thereby rendering them relatively unavailable for use in metabolic processes of various kinds. Specifically, said ions are thereby prevented from binding by or use by certain proteins and/or enzyme systems to support or cause specific processes in metabolic action. Exemplary proteins known to bind various ions are metal metalloproteinases (MMPs), which bind divalent cations such as zinc ($Zn+2$). The chelating effect of agents such as EDTA may inhibit the activity of MMPs by depriving the MMP of the $Zn+2$ ion (which is required for its function). Thus, the chelating agents (such as EDTA) in the antimicrobial agents of the present application may assist in controlling, inhibiting or avoiding tissue destruction caused by MMPs. Metallocarbamases also require divalent cations, e.g., zinc, and may be another target for EDTA or similar chelators. Other metalloproteases also are contemplated.

Zinc finger proteins are generally found as DNA binding protective proteins. They contain one or more short loop(s) with a conserved His-Cys motif binding generally one zinc ion per loop. They provide the DNA protective function by enwrapping the DNA molecule with a protein "glove" which it turn is held in place by one or more intercalated zinc fingers spaced along the DNA helix. Generally, zinc finger formation and stability can be disrupted by chelators such as EDTA, by binding and controlling the amount of free $Zn+2$, thus providing a means by which the antimicrobial agents of the present application have the potential to modify the degree of DNA protection from or exposure to other agents.

In addition, it is known that divalent ions, specifically $Mg+2$ and $Ca+2$ ions, must be present for the formation and/or maintenance of the lipopolysaccharide matrix that forms the bulk of biofilms. It is further known that EDTA imbues a solution with the power to disrupt or completely disintegrate an existing biofilm, and to retard or prevent their formation at least in the case of some medically significant biofilm forming organisms. It is therefore reasonable to suggest that inclusion of EDTA or other chelators in the antimicrobial agent of the present application, especially along with the other active ingredients, will be synergistically useful in biofilm prevention and eradication.

In applications where the possibility exists that the antimicrobial agent of the present application might come in contact with a patient's blood, it is desirable that the antimicrobial agent contain an anticoagulant. EDTA is often utilized in modern medical practice as an anticoagulant, for example as in blood draw tubes, e.g., Vacutainers® (Becton Dickinson and Company, Rutherford N.J.). Intravenous use is well known, e.g., in cases of metal chelation therapy to mitigate, among other things, heavy metal (as for example, lead, Pb) poisoning. The anticoagulant function of EDTA is thus an additional application to our antimicrobial agent of the present application, especially in blood-contact situations. Another significant advantage of EDTA inclusion in the antimicrobial agent of the present application is the case of a catheter lock solution, where contact with the patient's bloodstream is assured. EDTA is compatible with IV therapy, being also commonly utilized in treatment for heavy metal poisoning.

EDTA can be used in various forms, for example, as the pure acid, or, for example, as the disodium salt, or for example, the calcium disodium salt, dipotassium salt, or tetrasodium salt. In all these cases and others, the actual ionic composition of the EDTA in the antimicrobial agent of the present application will adjust, with the EDTA acting as a buffer, as the pH is adjusted. Furthermore, the EDTA provides a protective function in the antimicrobial agent of the present application solution, as in other known cases, by protecting the peroxide from divalent-catalyzed decomposition.

The present application provides the unexpected discovery that although EDTA has a relatively low solubility in solutions of, for example, ethanol, peroxide or peroxide-generating agents such as hydrogen peroxide ($H_2O_2$) can act as a powerful co-solvent. For example, in solutions of 50% v/v ethanol or higher, and at near-physiological pH but in the absence of $H_2O_2$, EDTA's solubility is limited to less than 10 mg/mL. However, when $H_2O_2$ is present, even at levels as low as 1-2%, stable solutions of EDTA at 10 mg/mL and at least 50-60% v/v ethanol are readily prepared and are stable (i.e., no precipitation or other changes are seen) at temperatures as low as 0° C. Furthermore, even in solutions of 50% v/v ethanol, EDTA in the presence of 6% $H_2O_2$, remained soluble at concentrations as high as 40 mg/mL, both at 27° C. and at 0° C. This unexpected effect is not due to the presence of additional water introduced with the $H_2O_2$, as evidenced by the fact that the effect occurs even when the total amount of water in the solution is held constant.

Thus, the unique combination of the individual ingredients in the antimicrobial agent of the present application provides relatively high concentrations of ethanol, high concentrations of EDTA and hydrogen peroxide levels that are unavailable by other means. The antimicrobial agent of the present application has unexpected stability, yet can be functionally powerful and versatile as an antimicrobial agent. Stability studies have shown shelf life lives (at room temperature) of 4% $H_2O_2$ solutions with high ethanol concentrations (50%) and high EDTA concentrations (10 mg/mL or greater) in excess of 14 months while retaining essentially all of the peroxide and alcohol effectiveness. The unexpected stability of EDTA against precipitation provided by the $H_2O_2$, and the stability of the hydrogen peroxide against decomposition, provided by EDTA is an example of synergy not normally seen in inanimate systems and resembles a symbiosis relationship. Additional chelators can be used to adapt the antimicrobial agent of the present application to specific applications. Examples of these may include but are not limited to dipicolinic acid, citrate, pyridine derivatives, various diamines or substituted diamines, and the like.

In addition to the unexpected stability, the relatively high concentrations of alcohol (such as ethanol) in the antimicrobial agent of the present application is able to deliver its killing power essentially unmitigated because of the unique properties conferred by the peroxide agent (such as $H_2O_2$) and the chelating agent (such as EDTA) in the combination. For example, some evidence exists that suggest penetration into a biofilm by $H_2O_2$ might be reduced because of the presence of peroxide-reactive agents, e.g., catalase or peroxidase, near the outer (distal) surface of the biofilm and that only reduced concentrations could penetrate deeply. The presence of ethanol in the antimicrobial agent of the present application can help mitigate the potential reduction of $H_2O_2$ penetration by an effect discovered by Mukergee et al. In some medical conditions, e.g., *Candida albicans*, the presence of ethanol can significantly reduce the thickness of the biofilm via the presence and action of the alcohol dehydrogenase (ADH) enzyme. The biofilm colonization of, for example, a catheter, is reduced. Further, ethanol is present in large concentration relative to both the enzyme and its cofactor, NADH. The consumption of ethanol will be severely limited, particularly because one of the mechanistic steps in the alcohol dehydrogenase utilizes free Zn+2 ion. Thus, in the combined action of the antimicrobial agent, EDTA—tying up zinc and simultaneously attacking the biofilm structure itself with limited NADH cofactor for ADH—only a small fraction of the total ethanol will be consumed, leaving the bulk remainder to act to penetrate the biofilm rapidly, delivering its killing power.

A viscosity-increasing agent (such as a thickener or gelling agent) might also be desirable. Exemplary viscosity-increasing agents include but are not limited to carboxymethyl cellulose (CMC), hydroxypropyl methylcellulose (HPMC), methyl cellulose, methyl hydroxyethyl cellulose (MHEC), hydroxyethyl cellulose, sodium hydroxyalkyl celluloses, and admixtures thereof. Other viscosity-increasing agents are contemplated, among them, but not limited to, silicone-based products such as dimethicone and silicone gels. An antimicrobial agent comprising hydroxypropyl methylcellulose (HPMC), preferably at a concentration of about 0.7% by volume is preferred.

Additional ingredients may be included in the antimicrobial agent of the present application. It is usually necessary to adjust the pH of the antimicrobial agent for particular applications. For example, in applications where the antimicrobial agent might be acidic on production, a base, typically but not exclusively sodium hydroxide solution, can be added to adjust the pH to the desired pH or to physiological pH. Alternatively, if the antimicrobial agent is basic when produced, an acid, typically but not exclusively either hydrochloric acid, citric acid, or acetic acid, can be added to return the pH to the desired pH or to physiological pH. In some embodiments, it might be desirable for the antimicrobial agent to be at some non-neutral or non-physiological pH, in which case additional adjustments would be made. In extreme cases, a far-from-neutral antimicrobial agent might be needed, in which case an additional buffer might be needed. Such buffers are well known to practitioners of the art and a variety is available for use.

The balance of the antimicrobial agent will be made up of water.

The antimicrobial agent composition (such as strength of ingredients) can be tailored to the specific needs of an individual. For instance, the composition can be dependent upon such factors as nature of the injury, depth of the wound, duration of time expired post injury, superinfection, vascularity and overall patient status (e.g., shock, renal failure, cardiorespiratory failure, coagulopathy). Alternatively, the antimicrobial agent of the present application can be applied in conjunction with medical dressings. Preferably, the dressing material can be a non-toxic material that will release the antimicrobial agent into the medical areas as desired. Appropriate dressing materials will depend upon the nature of the injury and the overall condition of the patient.

The antimicrobial agent of the present application may be preferable in solution form in certain applications. In other applications, the antimicrobial agent of the present application may be preferable in other forms, such as gel, cream, ointment, drops, injection, spray, solid forms such as tablets, and the like.

The antimicrobial agent of the present application may be administered as a bolus or as multiple doses over a period of time depending on the overall condition of the patient and medical attention needed.

The antimicrobial agent of the present application may be administered by many means including but not limited to topical application, intravenous injection, intraperitoneal injection or implantation, intramuscular injection or implantation, intralesional injection (e.g., within a tumor), subcutaneous injection or implantation, intradermal injection, suppositories, pessaries, enteric application, or nasal route. Preferably, the antimicrobial agent of the present application is administered by topical application.

The antimicrobial agent of the present application may be administered to many areas including but not limited to a wound site (including skin around wound areas), a catheter site, a surgical site, an injection site, a catheter, a catheter lumen, a thermal burn site, a chemical burn site, a radiation burn site, a skin lesion (abrasions), oral sites (such as leukoplakias, carcinomas-in-situ, oral carcinomas, "canker sores" (i.e., open lesions), bony sites (with osteomyelitis, for example, caused by *Staphylococcus aureus, Pseudomonas aeruginosa, Acinetobacter baumannii*), anal sites, vaginal sites, cervical sites, vulvar sites, penile sites, ulcerated skin sites (e.g., diabetic foot ulcers, decubiti ("bed sore") sites), acne sites (e.g., facial, trunkal, and others), actinic keratosis sites, inflamed sites, irritated sites, gastric sites, gastrointestinal sites (upper and lower), esophageal sites, esophagogastrointestinal sites, intestinal sites, cardiac sites, vascular sites, nasal sites, nasopharyngeal sites, and aural sites and a catheter locking solution.

Examples of Applications for the Antimicrobial Agents

The antimicrobial agent of the present application may be provided to inhibiting or reducing microbial growth. The antimicrobial agent of the present application may also be provided to inhibit or reduce microbial growth.

The antimicrobial agent of the present application may be provided to inhibiting or reducing microbial infections. The antimicrobial agent of the present application may also be provided to inhibit or reduce microbial infections.

The microbial growth or microbial infections may be due to different microorganism including but not limited to a bacterium, a fungus, a protozoa and a virus. In certain applications, the microbial growth or microbial infection may be associated with a medical device including but not limited to catheters, stents, medical implants, dental devices and implants, prosthetic devices and implants, and cardiac devices and implants.

It is also contemplated that the antimicrobial agent of the present application may be provided to certain critical surfaces external to the subject or patient's body but in positions wherein ready access by pathogenic microorganisms to the subject or patient's tissues or bloodstream is available. Such sites include, without limitation, catheter lumens, catheter insertion sites, and catheter ports. Intravenous equipment and the like are also candidates for use. In addition, wounds, burns, skin lesions and vesicles, oral, cervical, vaginal, vulvar, penile, anal sites, esophageal sites, gastric sites, gastrointestinal sites, esophagogastrointestinal sites, intestinal sites and the like are contemplated as intended use locations for the antimicrobial agent of the present application. For example, it is contemplated that the antimicrobial agent of the present application may be provided to such sites by endoscopy or radiological tube placement and intraluminal infusion.

The antimicrobial agent of the present application may be applied as an immunomodulator such that it interacts with matrix metalloproteinases (MMPs) or other cytokines or chemokines to modulate the degree of interaction between these naturally occurring substances and the underlying tissues. Over expression of these naturally occurring substances may cause undesirable or harmful inflammation and other disturbances associated with healing or recovery from trauma or illness.

Accordingly, it is contemplated that the antimicrobial agent of the present application may be used to adjust or alter the amounts, levels or activities of the MMPs, cytokine or chemokine, or TNF-alpha blockers, generally by a chemical interaction. For example, MMPs are so named because they require the presence of at least one divalent metal ion, generally Zn+2, for their function. One component of the antimicrobial agent of the present application is designed to coordinate or chelate with multivalent metal ions, thus preventing them from being available for use by the MMPs. For example, Tumor necrosis factor (TNF)-alpha converting enzyme (TACE) is a MMP and the key sheddase that releases TNF-alpha from its inactive cell-bound precursor. The activity of TACE may be severely disrupted by the lack of multivalent metal ions that have been sequestered by the chelating component of the antimicrobial agent of the present application. This, in turn, would reduce the amount, level and activity of active TNF-alpha and the associated proinflammatory effects of TNF-alpha. Similarly, another component of the antimicrobial agent of the present application is designed to provide an oxidative function to some portions of enzymatic molecules, providing a means by which they are inactivated or denatured. This oxidative function causes sulfur-bearing amino acids in the enzyme structures to be oxidized, a change which is reflected by changes in the charge-bearing, the H-bonding, the solvent-bonding and hydration properties, and consequently, the overall folding configuration and shape of the protein, causing significant changes in its catalytic properties. It is further contemplated that the oxidative component of the antimicrobial agent of the present application may cause sulfur-bearing amino acids common in pro-inflammatory cytokines and chemokines (such as IL-8, IL-12, IL-6 and TNF-alpha) to be oxidized, which may significantly alter the levels and activities of these proteins.

In addition to the synergistic effect on the chelation and oxidative functions provided by the antimicrobial agent components, it also has the ability to provide solvent interactions that can modify the hydration, the H-bonding, and the hydrophilic/hydrophobic balance of the overall bio-environment. Such changes can be important in, for example, modifying various membranes that are important to pathogenic organisms, and perhaps even in modifying the structure of viruses or their virulence by modifying their target membranes of bacteria even of eukaryotic cell targets, for example, the endoplasmic reticulum (ER) of mitochondria. Similarly, such changes are also significant in that they can effect, often by disrupting, the intercellular and/or the intracellular signaling of prokaryotes and eukaryotes, including multi-cellular organisms, including humans. In higher organisms, including humans, such chemical signaling can be involved in many conditions including, for example, cancers, either in the carcinogenic stages, in the development of cancers or in the metastatic stages. The arsenal of effects provided by the antimicrobial agent of the present application is of value in controlling the chemical communication in such organisms.

It is further contemplated that the antimicrobial agent of the present application may adjust or alter the amounts, levels or activities of the MMPs, cytokines and chemokines via its nucleophilic interaction. For example, the EDTA in the antimicrobial agent of the present application may play a role not only in the chelation of metal ions but may also exert nucleophilic activity attributable to its two amino groups. The nucleophilic activity of the EDTA may result in disruption of peptides of various biomolecules, particularly proteins such as cytokines and chemokine, and thereby disrupt their function. In addition, the S—S linkage that creates the "loops" and "hairpin" turns in proteins may also be readily disrupted by nucleophiles, thereby altering the complex 3-D structure and its actions. Proteins that contain the amino acid methionine are also subject to 3-D structure modifications by the oxidative action of $H_2O_2$, readily converting the Met-S-R group to the Met-S(=O)—R group, which has significantly different polarity, shape and solvent interactions. Thus, the antimicrobial agent of the present application may modify and disrupt the structures of many biomolecules causing significant changes to their activities and functions. Such disruption of, for example, MMP activity and function may significantly affect many downstream conditions, including, tumor formation, tumor progression, tumor metastasis and angiogenesis. MMPs have been well characterized as being key players in multiple steps of cancer, either at the carcinogenic stages, developmental stages or metastatic stages.

The antimicrobial agent of the present application may be used to inhibit or reduce an immune response, generally by inhibiting cytokine or chemokine levels or activity and/or cytokine or chemokine receptor levels or activity. This can be achieved by many means including but not limited to chemical inhibition or modification of the cytokine or chemokine and/or its receptor.

The antimicrobial agent of the present application may also provide a means by which other potentially harmful components in a war wound, trauma, burn or other healing area are inactivated and tissue injury and systemic toxicity are reduced. These components include but not limited to host MMPs, TNF-alpha, bacterial beta-lactamases, (including multi-resistant extended spectrum beta-lactamases (ESBL)), carbapenemases, and metallocarbamases. The components are generally relatively complex protein-based compounds. However, the antimicrobial agents of the present application provides a spectrum of biochemical reactions, at least one or more of which will be effective at disrupting and/or attenuating the harmful processes. Healing rates and/or the general well-being of the subject will be improved by a reduction in the adverse effects seen from host over-expression of cytokines, chemokines and other inflammatory molecules. Preservation of therapeutic activity of systemic antimicrobials, by preventing microbial enzymatic inactivation and lowering of bacterial and fungal toxins, will also augment host survival.

Accordingly, the antimicrobial agent of the present application may also be provided to inhibit or reduce an inflammatory condition. The antimicrobial agent of the present application may also be provided to treat an inflammatory condition. In some cases, the inflammatory condition is associated with microbial growth or microbial infection. In other cases, the inflammatory condition is associated with a medical device.

The over-expression of cytokines, chemokines and other inflammatory molecules during an inflammatory reaction induced as a result of, for example, microbial infections, may further contribute to the initiation, development and/or progression of downstream conditions or diseases.

For example, chronic inflammation has also been associated with the development of cardiovascular diseases and related disorders. Studies of the inflammation paradigm in coronary pathogenesis suggest that chronic infections may be involved by releasing cytokines and other pro-inflammatory mediators (e.g., C-reactive protein (CRP), tumor necrosis factor (TNF-alpha)) that may in turn initiate a cascade of biochemical reactions and cause endothelial damage and facilitate cholesterol plaque attachment. Recent studies suggest that patients with elevated basal levels of C-reactive protein (CRP) are at an increased risk of cardiovascular disease (such as atherosclerosis), hypertension and diabetes. CRP is an acute-phase protein found in the blood, the levels of which rise in response to inflammation. It is commonly used as a marker of inflammation and infection.

There are also studies showing that periodontal diseases may increase the risk of cardiovascular disease and that the risk is even greater for stroke. Epidemiological studies suggest that inflammation may be the link between periodontal diseases and the cardiovascular complications. Interestingly, in patients with chronic periodontitis, elevated levels of CRP have been detected in association with an increased risk of developing atherosclerosis. Periodontal therapy has been shown to produce significant modulation of CRP levels and this may benefit individuals with cardiovascular diseases. It is contemplated that the periodontal therapy provided by the antimicrobial agent of the present application would be effective in individuals with or at risk of developing cardiovascular diseases. Accordingly, the antimicrobial agent of the present application may be useful for treating cardiovascular diseases and related disorders or reducing the risk of developing cardiovascular diseases and related disorders.

It has also been suggested that inflammatory activity may play a key pathogenic role in insulin resistance and diabetes. For example, the inflammatory biomarker CRP has been used to monitor insulin resistance and cardiovascular risk in diabetic and nondiabetic individuals. A growing number of clinical trials have tested the hypothesis that antidiabetic drugs specifically targeting insulin resistance could benefit individuals by reducing inflammation, atherogenesis, and thus cardiovascular risk. The clinical study results underline the benefit of an early insulin resistance treatment to oppose systemic vascular inflammation and cardiometabolic syndrome in patients with elevated levels of CRP. Accordingly, the antimicrobial agent of the present application may be useful for treating diabetes and related disorders or reducing the risk of developing diabetes and related disorders.

Chronic inflammation has also been shown to play an important role in tumorigenesis, suggesting that negative regulation of inflammation is likely to be tumor suppressive. For example, one mediator that is involved in systemic inflammation and induces apoptotic cell death is tumor necrosis factor (TNF-alpha). The primary role of TNF-alpha is in the regulation of immune cells. It is able to induce apoptotic cell death, to induce inflammation, and to inhibit tumorigenesis and viral replication. Dysregulation of TNF-alpha production has been implicated in a variety of human diseases, including cancer. Thus, modulation of the activity of inflammatory mediators, such as TNF-alpha, may have beneficial implications in regulating the inflammatory-mediated carcinogenesis. Alternatively, modulation of TNF-alpha converting enzyme (TACE), which releases active TNF-alpha, may also have beneficial implications in regulating inflammatory-mediated carcinogenesis. It is contemplated that the antimicrobial agent of the present application would be effective in individuals with or at risk of developing cancer. It is further contemplated that cancers at various carcinogenic stages, either in the precancerous stage, during the development of cancers or in the metastatic stages are included within the present application.

p53 (also known as protein 53 or tumor protein 53) is another well-known mediator that is a tumor suppressor/pro-apoptotic protein important in multicellular organisms. It regulates the cell cycle and, thus, functions as a tumor suppressor that is involved in preventing cancer. p53 is also a general inhibitor of inflammation that acts as an antagonist of nuclear factor kappaB (NFkappaB). Studies have shown that p53, acting through suppression of NFkappaB, plays the role of a general "buffer" of innate immune response in vivo that is well consistent with its tumor suppressor function. This provides further evidence that immunomodulation may be an effective approach to mitigate or treat inflammatory-mediated carcinogenesis. It is contemplated that the antimicrobial agent of the present application would be effective in individuals with or at risk of developing cancer. It is further contemplated that cancers at various carcinogenic stages, either in the precancerous stage, during the development of cancers or in the metastatic stages are included within the present application.

The pro-apoptotic effects of p53 have also been associated with human papillomaviruses (HPVs) and the development of cancer. For example, the HPV type 16 oncoprotein, E6, complexes with and promotes degradation of p53. Interestingly, HPV type 16 also appears to play a role in the development of certain malignancies. It is contemplated that apoptotic mediators may be involved in the regulation of cancer and that immunomodulation may be an effective approach.

The role of epidermal growth factor (EGF) and vascular endothelial growth factor (VEGF) in tumorigenesis has also been well documented. EGF is involved in the regulation of cell growth, proliferation and differentiation. Upregulation of EGF/EGFR (epidermal growth factor receptor) activity leads to uncontrolled cell division, a predisposition to the development of cancer. VEGF is produced by cells that stimulate the growth of new blood vessels, a process known as angiogenesis. Angiogenesis is necessary for the growth and metastasis of tumors and inhibition of VEGF impairs angiogenesis and disrupts metastatic spread. It is contemplated that immunomodulation may be an effective approach to regulate the development and/or progression of cancer initiated or mediated by the EGF and/or VEGF pathways. Interestingly, studies have demonstrated that ethanol can induce structural and functional alterations of the EGFR molecule, resulting in decreased EGF receptor binding, and thereby impairing its receptor kinase activity and its physiological function. Thus, it is contemplated that the ethanol alcohol component within the antimicrobial agent of the present application may be effective in regulating the development and/or progression of cancer via modulation of the activity of the EGFR molecule.

The present application demonstrates that the antimicrobial agent of the present application was able to modify and significantly and rapidly improve the course of leukoplakia (a pre-malignant lesion) or cancer, either in the carcinoma-in-situ stage or in the invasive carcinoma stage. The development of the leukoplakia was in an infected area of the subject diagnosed with chronic periodontitis, an inflammatory condition characterized by chronic inflammation of the periodontal tissues that is caused by accumulation of profuse amounts of dental plaque. Chronic periodontitis is initiated Gram-negative and Gram-positive tooth and gingival-associated microbial biofilms that elicit a host response, which results in bone and soft tissue destruction. This disease is associated with a variable microbial pattern. In response to endotoxin derived from periodontal pathogens, several osteoclast-related mediators target the destruction of alveolar bone and supporting connective tissue such as the periodontal ligament. Some major drivers of this aggressive tissue destruction include matrix metalloproteinases (MMPs), cathepsins, and other osteoclast-derived enzymes. Although sub-antimicrobial doses of antibiotics have been used to alter host response to the periodontal pathogens, it has been demonstrated that topical treatment using doxycycline or minocycline antibiotics leads to resistance of not only oral flora, but may colonize the patient in other body sites for potential infection. Chlorhexidine oral application selects out more resistant bacteria, e.g., methicillin resistant *Staphylococcus aureus* (MRSA), which could lead to persistent inflammation and transmission of resistant pathogens. The present application demonstrates that the antimicrobial agent was effective at inhibiting and treating the leukoplakia condition and forms of squamous cell carcinoma, which are likely secondary manifestations induced by the cytokines, chemokines and other inflammatory molecules present during an inflammatory reaction.

The role of viruses (and viral infections) in the pathogenesis of cancers is another important medical research area. Human papilloma virus (HPV) is a member of the papillomavirus family of viruses that is capable of infecting humans. HPV infections occur in the stratified epithelium of the skin or mucous membranes (such as in the cervix, vulva, vagina, penis, anus and oropharyngx). Persistent infection with "high-risk" HPV types may progress to precancerous lesions and invasive cancer. A growing number of studies have shown a link between HPV infection and certain types of cancers (such as penile and anal cancers). Further studies have also shown a link between a wide range of HPV types and squamous cell carcinoma of the skin. It is contemplated that effective treatment of the leukoplakia condition (a form of squamous cell carcinoma) using the antimicrobial agent of the present application may be mediated, in part, by its effect on any possible underlying viral infection or activity. The effect may also be mediated by any possible underlying inflammatory activity.

Interestingly, the E6 and E7 proteins of HPV have been associated with promotion of dysplasia and squamous cell carcinoma. In particular, the E6 protein is involved in numerous activities including inactivating p53, blocking apoptosis, activating telomerase, disrupting cell adhesion, polarity and epithelial differentiation, altering transcription and reducing immune recognition. The E6 protein contains four cysteine arrays that constitute two relatively large zinc fingers, both of which are required for full function. It is contemplated that the antimicrobial agent of the present application may disrupt the zinc finger formation and stability of the E6 protein through its chelating function in sequestering and binding of free $Zn+2$ ions. This may provide an effective means for inhibiting or treating HPV-mediated carcinomas.

Another example of the role of viruses in the pathogenesis of cancers is demonstrated by the Epstein-Barr virus (EBV), also called human herpes virus 4 (HHV-4). It is known to be a cancer-causing virus of the herpes family, and is one of the most common viruses in humans. There is strong evidence that the virus has a primary role in the pathogenesis of multiple cancers, particularly Hodgkin's disease, Burkitt's lymphoma, nasopharyngeal carcinoma, and central nervous system lymphomas associated with HIV. In cases of nasopharyngeal carcinoma, it is contemplated that the antimicrobial agent of the present application would be an effective means for inhibiting or treating the carcinoma via its effect on any possible underlying viral infection or activity. The effect may also be mediated by any possible underlying inflammatory activity.

The antimicrobial agent of the present application may further provide a means of significantly reducing the severity and shortening the course of "cold sores" likely resulting from an outbreak of Herpes simplex. Accordingly, the antimicrobial agent of the present application may also be provided to inhibit or reduce a viral condition or disease. The antimicrobial agent of the present application may also be provided to treat a viral condition or disease.

Another contemplated application of the antimicrobial agent of the present invention may be for the inhibition and/or treatment of canker sores (aphthous), a type of oral ulcer, which presents as a painful open sore inside the mouth or upper throat and is characterized by a break in the mucous membrane. Once thought to be a herpes virus infection, the entire class of canker sores is now thought to be an aggregate of a variety of disease processes, each with the ability, in its own way, to produce rapid but self-limiting destruction of mucous membranes, predominantly through immunologic and ischemic mechanisms. In some individuals the ulcers are a secondary or hypersensitivity response to antigenic stimulus, especially foods), while in others they are a primary autoimmune disorder. It is contemplated that the antimicrobial agent of the present application may be useful for the inhibition and/or treatment of canker sores. The effect may be mediated by modulation of any underlying viral infection or activity or inflammatory activity.

It is contemplated that the antimicrobial agent of the present application may be used as adjunctive therapy in combination with existing therapies. The term "adjunctive" is used interchangeably with "in combination" or "combinatorial" and are used where two or more therapeutic or prophylactic regimens affect the treatment or prevention of the same disease. For example, the antimicrobial agent of the present application may be used as adjunctive therapy for the management of cancer. The antimicrobial agent of the present application may provide synergistic effects, both in anti-cancer efficacy and in control or reduction of side effects, such as toxicity from chemotherapy or radiation therapy and chemoresistance. The antimicrobial agent of the present application may provide a means of adjusting (e.g., reducing) the dosages from the existing therapies such that the desired effect is obtained without meeting the threshold dosage required to achieve significant side effects. For example, the antimicrobial agent of the present application may be used as an adjunctive therapy to radiation therapy which creates hydroxyl radicals and DNA damage to cancer cells, by potentially reducing the dose and/or duration of radiotherapy and increasing efficacy with reduced toxicity. It is contemplated that such adjunctive treatment may be achieved by way of simultaneous, sequential or separate dosing from the existing therapies.

Accordingly, the antimicrobial agent of the present application may also be provided to inhibit or reduce a condition or disease resulting from or associated with microbial growth or infection. The antimicrobial agent of the present application may also be provided to treat a condition or disease resulting from or associated with microbial growth or infection. Such conditions may include but is not limited to inflammatory diseases, viral diseases and cancer or pre-cancerous conditions.

The antimicrobial agent of the present application may provide a means for altering the chemical environment of target areas of human and animal patients, especially in wounds, burns, surgical sites, and catheter insertion sites, to prevent cell damage and/or toxicity by the presence of a range of materials that are commonly found at such sites. Such materials often have a balance of beneficial and deleterious effects, depending on their concentrations and other factors. They are usually present in very low levels, generally in the micromolar or even at the nanomolar levels ($10^{-9}$) levels, and in some cases picomolar ($10^{-12}$) levels. Accordingly, this application provides a series of reactive possibilities at such levels because the combination of components in the antimicrobial agent are present at significantly higher levels (i.e., millimolar or molar), which has the effect of driving reactions, which would otherwise seem to be unfavorable, further towards completion.

It is contemplated that the antimicrobial agent of the present application may be provided to target sites by means of a medical device. Medical devices may be treated or coated with the antimicrobial agent of the present application and incorporated into medical and dental instruments including disposable or permanent or indwelling catheters (e.g., central venous catheters, dialysis catheters, long-term tunneled central venous catheters, short-term central venous catheters, peripherally inserted central catheters, peripheral venous catheters, pulmonary artery catheters, urinary catheters, and peritoneal catheters), urinary devices, vascular grafts, vascular catheter ports, wound drain tubes, ventricular catheters, hydrocephalus shunts, heart valves, heart assist devices (e.g., left ventricular assist devices), pacemaker capsules, incontinence devices, penile implants, vulvar devices, small or temporary joint replacements, urinary dilator, cannulas, elastomers, hydrogels, surgical instruments, dental instruments such as dental trays, tubings, such as intravenous tubes, breathing tubes, adhesives (e.g., hydrogel adhesives, hot-melt adhesives, silicone-based adhesives or solvent-based adhesives), bandages, orthopedic implants, and any other device used in the medical and dental field. Medical devices also include any device which may be inserted or implanted into a human being or other animal, or placed at the insertion or implantation site such as the skin near the insertion or implantation site. Medical devices further include surfaces of equipment in operating rooms, emergency rooms, hospital rooms, clinics, and bathrooms.

It is also contemplated that the antimicrobial agent of the present application may be effective as a spermicidal and antimicrobial agent, which could help prevent the spread of sexually transmitted diseases. Prevention of HPV transmission, along with vaccines, may markedly reduce cervical cancer, as well as some vulvar and oral pharyngeal carcinomas. The antimicrobial agent of the present application may be administered alone or in combination with one or more barrier methods of contraception, such as a diaphragm, sponge or condom.

The antimicrobial agent of the present application may be utilized as a cleaner/antiseptic when applied to hands to reduce or prevent the transmission of bacterial, fungal, viral and parasitic diseases, especially in a clinical environment.

The antimicrobial agent of the present application may provide a means by which biofilms as formed by bacterial and fungal organisms are disrupted and the embedded organisms in the biofilm, whether they are biofilm formers or present by accidental inclusion, entrapment or otherwise, are killed or rendered non-viable and/or otherwise non-threatening.

The antimicrobial agent of the present application may provide a means by which bacterial and yeast spores are either killed outright in the spore stage, or are rendered ineffective by being unable to germinate, or by germination followed by rapid killing before their pathogenic potential is expressed.

The antimicrobial agent of the present application may provide a means by which quorum sensing (QS) mechanisms used by biofilm forming microorganisms is interrupted. While these mechanisms vary from organism to organism, and gram-positive organisms use a somewhat different QS system from gram-negative, in all cases there is a molecule or series of molecules which provide the QS function. In many cases, these are protein molecules that are potentially susceptible to structural changes by reaction with the antimicrobial agent of the present application. Reactions such as hydrolysis, alcoholysis, esterification, transesterification, oxidation, protein denaturation, or chelation of both free ions and partially bound cations are likely possibilities. Substances which are targets for hydrolytic or alcoholytic destruction or disruption are, for example, acyl homoserine lactones (AHL's, the QS molecules of gram-positive biofilm formers), and other lactone or ester components of gram-positive bacteria. Biofilms area are also known to be disrupted by chelators, which it is believed, results from the binding effect of the chelator on divalent, trivalent or other cations necessary for the formation of the biofilm. Inclusion of one or more chelators, generally preferred but not limited to EDTA, provides this function to the antimicrobial agent of the present application.

*Candida albicans*

As biofilm studies proliferate and as their importance in human and animal pathogenesis becomes more widely recognized, other points of vulnerability become known. Often, these studies are organism-specific and thus their potential for generalized medical applications is not known as yet. On the other hand, some involve such important pathogens that even a narrow range of applicable species provides a window into medically important treatments. For example, Mukherjee et al. have shown that the enzyme alcohol dehydrogenase (Adh1p) restricts the ability of *Candida albicans* to form biofilms on catheter surfaces via an alcohol-based mechanism. Interestingly, although the Adhlp enzyme is necessary for the formation of the biofilm, once the biofilm is produced by the planktonic *C. albicans* cells, the production of Adhlp is significantly reduced relative to the planktonic quantity. Also interestingly, they found a significant change in the chemical activity of the Adhlp's conversion of acetaldehyde into ethanol when comparison was made between planktonic and biofilm *C. albicans*. In the planktonic form the enzyme is producing larger quantities of ethanol whereas in the biofilm acetaldehyde quantities rise significantly. This finding seems to imply that the biofilm-bound Adhlp is unable to process the acetaldehyde to ethanol, but does not explain the mechanism of the phenomenon. We can speculate, however, that by limiting the amount of ethanol in the biofilm, the *C. albicans* are down-regulating the Adhlp activity which in turn fosters additional biofilm growth. The antimicrobial agent of the present application is designed with a high level of ethanol, which alone provides significant activity against *C. albicans* through a Mukherjee-effect reduction of biofilm formation. In addition, our combinations of ingredients have already been shown to be quickly active against planktonic *C. albicans* (unpublished data). This combination of high-level killing of planktonic cells and the ability to assist in prevention of biofilm formation by the few remaining viable cells would be expected to provide a patient with very substantial protection against *Candida* infection of catheters and other implanted devices.

This hypothesis is supported by the work of Baillie and Douglas. Their work developed physical conditions for growing *Candida* biofilms of maximal thickness and density and a study of the chemical composition of them. Under static conditions, the formation of a biofilm matrix is minimal but is greatly enhanced by the presence of a liquid flow. It is of interest that they found that the extent of the matrix formation did not affect the susceptibility of the biofilms to different anti-fungal drugs, including flucytosine and three azole compounds, even at levels representing many multiples of the planktonic MIC.

The independence of susceptibility by differing thicknesses/densities of the biofilm matrix is verified by Andes et al. where in *Candida*, they also cite data showing the importance of controlling or eliminating infections. Most of the candidemia cases involve catheters, and in the largest reported study, 71% these cases implicated a catheter. In catheter-related *Candida* bloodstream infections, 41% mortality was seen in patients whose catheter was retained. Andes et al. also stress that they observed a significant difference in the biofilm forming behavior of *Candida* depending on the surface material of the catheter or other plastic substrate. Even similar polymeric materials, e.g., polyvinylchloride (PVC) exhibited differences when provided by different manufacturers.

This work is of particular interest to the Assignee in that the original application all involves medical devices wherein the flow of liquid is either minimal or non-existent. In those cases, where the biofilm matrix is not stimulated by flow, the tendency will be for the microorganisms to remain planktonic and therefore more vulnerable to the solution.

*Staphylococcus aureus*

Another species receiving much medical attention recently and which potentially provides an alternative window into biofilm prevention or mitigation is *Staphylococcus aureus*. In particular MRSA, i.e., methicillin resistant *S. aureus*, is particularly troublesome and dangerous. Caiazza and O'Toole have shown that the cell-to-cell interaction promoter alpha-toxin, also called alpha-hemolysin, is required for biofilm formation. Other substances such as autolysin, teichoic acids and surface proteins are integral to the early formation of biofilm colonization, but alpha-toxin is essential. It appears that the alpha-toxin is required for the synthesis of polysaccharide intracellular adhesion (PIA). Alpha-toxin has been known for some time (see, for example, Bhakdi S, Tranum-Jensen J) and has been characterized as a hydrophilic protein, MW=34 kD, and which is shown to be a pore-former for the surface membranes of the organism.

In the application of the antimicrobial agent of the present application to mitigation of *S. aureus* biofilms, we would primarily expect that hydrogen peroxide would attack the alpha-toxin structure by oxidative breaking of S—S bonds, oxidation of methionine methylthioether to sulfoxide, oxidation of free amino-groups and free hydroxide groups and thus disrupt the folding of the protein. Such changes would likely also disrupt the ability of the alpha-toxin to encourage biofilm formation. Other gram-positive bacteria, such as *Streptococcus* species, with some similar cell membrane structures, toxins and biofilms could be expected to be susceptible to the action of the antimicrobial agent of the present application.

Gram-Negative Bacteria, Including *Escherichia coli*, *Klebsiella* and *Pseudomonas aeruginosa*

Lipopolysaccharide, often called Lipid A, is an endotoxin known to be a controlling factor necessary to the biogenesis of membrane lipids. Lipid A is one of the highly toxic components released on the death of some bacterial cells and causes toxic shock in some cases. The structure of Lipid A is known (see, for example, Jia et al.). While the general core structure is essentially invariant, a number of species-dependent modifications are known. One highly hydrophobic section is formed from a series (usually four chains) of fatty acyl esters or amides of the either sugar-ring-bound OH's or sugar-ring bound NH's. These four chains have hydroxyl groups in the 3' positions, which are often also acylated, generating a large hydrophobic zone in the molecule, usually with two additional chains. Jia et al. report that one of the hydroxy groups participates in the lipid trafficking across the outer bacterial membrane (OM) by forming a palmitoyl ester at the 3' hydroxide. The formation of the palmitoyl ester provides a protective function, preventing host immune system attack, and controlling endotoxin formation.

This approach should be able to avoid the rapid generation of resistance by the bacteria since it does not provide selective pressure for resistance development. Stopping or interfering with a fundamental process leading to biofilm formation, could prevent a simple mutation or simple series of mutations to bypass or counteract the genesis of biofilm. It is also important to note that the hypothesized process takes place in the presence of the antimicrobial agent of the present application which has already been shown to be toxicidal to the broad spectrum of tested microorganisms, including biofilm formers, non-biofilm formers and spores. For example against Bacillus cereus spores, the antimicrobial agent of the present application quickly caused a rapid sporicidal reduction of greater than 6-log colony forming units (CFU) (unpublished results). Because of the multitude of different physicochemical reactions triggered by the antimicrobial agent of the present application, survival of vegetative organisms or spores, even in protective biofilms, would be extremely unlikely or more particularly, to reproduce. Additionally, the probability for development of genetic resistance would be even lower. Since the therapy of the antimicrobial agent of the present application may include topical application and does include antimicrobials agents used in systemic therapy, the antimicrobial agent of the present application would not promote resistance to commonly used systemic antimicrobials.

Other effects relating to biofilms and their formation are candidates for the antimicrobial agent of the present application. For example, as mentioned above, biofilms, once formed, are able to reduce the effectiveness of many known antibiotics by several orders of magnitude, compared to the therapeutic levels for planktonic forms of the same species. This problem is exacerbated in the case of some bacteria by the fact that they change their phenotypic presentation during and after the formation of the biofilm. For example, Pseudomonas aeruginosa displays multiple phenotypes during biofilm development, in fact at least four stages were identified including one stage which involves the development and use of flagella not present in other phenotypes. Thus, in addition to the potential resistance to "traditional" antibiotics because of the presence of the physiochemical effects of the biofilm itself, it is clear that a range of endogenous changes in gene expression are occurring, thus complicating the use of traditional antibiotics or the search for new ones. The effect of changing the expression of portions of the genome can also change the degree of diversity within a given species of biofilm, even though no external stress or mutagen is applied. Such "variants", as shown by Boles and Singh are generated by biofilms of *Pseudomonas aeruginosa, Pseudomonas fluorescence, Vibrio cholera, Staphylococcus pneumonia* and *Staplylococcus aureus*. They appear to be produced from wild-type (WT) organisms which are subject to endogenous oxidative stress. Addition of anti-oxidants, e.g., N-acetyl cysteine or L-proline reduced or eliminated the ability of WT to produce the variants. And, to reiterate, fewer variants result in easier-to-control biofilms. Thus it might be necessary to "fine-tune" the antimicrobial agent of the present application in some cases, particularly where the target organisms might be responding to the original treatment of the antimicrobial agent of the present application by generating variants. Cantin and Woods showed that hydrogen peroxide can act in vitro with chloride ion (C1-1) to generate hypochlorous acid (HOCl), which in turn can react to form chloramines species in the presence of aminoglycosides like tobramycin or gentamicin. Using 5-thio-2-nitrobenzene as a model compound for sulfur-based oxidative stress or oxidative damage, they found that dimethyl sulfoxide (DMSO) added to a solution containing HOCl protected the 5-thio-2-nitrobenzene from oxidation, but DMSO was unable to provide the same protective action in the presence of gentamicin or tobramycin. Since DMSO is known to have minimal toxic and other disruptive effects to humans in low concentrations, DMSO and similar compounds represent potential additives to the antimicrobial agent of the present application to fine-tune its oxidative properties. Similarly, it has also been shown that the oxidant products are hydrophilic. In the case of the antimicrobial agent of the present application, then, the ethanol fraction of the mixture would become relatively more hydrophobic because of the migration of hydrophilic materials (i.e., ions and the like), towards the aqueous phase. The ethanol thus "freed" would become more penetrating and more toxic to the lipid fractions, including the cell membranes or cell walls of the biofilm formers and their EPS "fortress". Additional deleterious effects on bacterial quorum sensing, bacterial cytotoxicity and proliferation and biofilm formation would be expected.

In intravenous infusion therapy involving catheters, clotting avoidance and maintenance of sterility on the inner surfaces of the catheter port and lumen is essential. For that reason, use of flush solutions and lock solutions has become the standard of practice. The antimicrobial agent of the present application, in one embodiment, is a useful catheter lock solution. In this embodiment, the ingredients list would exclude any thickener or gellant and would reduce the peroxide level to approximately 0.5%-1.0%.

The present application is further illustrated by the following specific examples. The examples are provided for illustration only and should not be construed as limiting the scope of the application in any way.

EXAMPLES

Example 1

Preparation of the Antimicrobial Agent

The antimicrobial agents of the present application were prepared by mixing a low molecular weight alcohol, such as ethanol, a peroxide or peroxide-generating agent, such as hydrogen peroxide, and a chelating agent, such as EDTA, at various concentrations.

Briefly, the desired amount of dry disodium EDTA dehydrate was measured and added to a 50 mL flask. Next, the desired amount of hydrogen peroxide ($H_2O_2$) was added to the EDTA along with the desired amount of sterile water. The test solution was mechanically mixed until the EDTA had completely dissolved, during which the pH was monitored. Once the test solution appeared translucent, the test solution was adjusted to a pH of ~7.4 using the desired amount of 1.0 M NaOH. Next, the desired amount of ethanol was slowly added (dropwise) to the test solution until complete dissolution. The resulting test solution was again adjusted to a pH of ~7.4, if necessary, using the desired amount of 1.0 M NaOH. Sterile water was added, if necessary, until the total weight was approximately 40.00 g.

Table 1 illustrates the properties resulting from the different combinations in the antimicrobial agents of the present application.

TABLE 1

| EtOH (% v/v) | $H_2O_2$ (% v/v) | EDTA (mg/mL) | Properties |
|---|---|---|---|
| 50 | 0 | 10 | Precipitation formed |
| 50 | 0 | 15 | Precipitation formed |
| 50 | 0 | 25 | Precipitation formed |
| 52 | 0 | 15 | Precipitation formed |
| 54 | 0 | 10 | Precipitation formed |
| 58 | 0 | 10 | Precipitation formed |
| 60 | 0 | 10 | Precipitation formed |
| 60 | 0 | 20 | Precipitation formed |
| 25 | 0.5 | 15 | No precipitation |
| 50 | 0.5 | 7.5 | No precipitation |
| 25 | 1 | 10 | No precipitation |
| 50 | 1 | 10 | No precipitation |
| 56 | 1 | 10 | No precipitation |
| 60 | 1 | 20 | No precipitation |
| 50 | 1.5 | 5 | No precipitation |
| 50 | 1.5 | 10 | No precipitation |
| 50 | 1.5 | 15 | No precipitation |
| 35 | 2 | 20 | No precipitation |
| 58 | 2 | 10 | No precipitation |
| 60 | 2 | 20 | No precipitation |
| 50 | 3 | 10 | No precipitation |
| 54 | 3 | 10 | No precipitation |
| 60 | 3 | 10 | No precipitation |
| 60 | 3 | 20 | No precipitation |
| 35 | 4 | 20 | No precipitation |
| 50 | 4 | 10 | No precipitation |
| 56 | 4 | 10 | No precipitation |
| 60 | 4 | 20 | No precipitation |
| 35 | 5 | 20 | No precipitation |
| 50 | 5 | 7.5 | No precipitation |
| 50 | 5 | 9 | No precipitation |
| 50 | 5 | 10 | No precipitation |

TABLE 1-continued

| EtOH (% v/v) | $H_2O_2$ (% v/v) | EDTA (mg/mL) | Properties |
|---|---|---|---|
| 54 | 5 | 10 | No precipitation |
| 56 | 5 | 10 | No precipitation |
| 20 | 6 | 40 | No precipitation |
| 40 | 6 | 40 | No precipitation |
| 50 | 6 | 40 | No precipitation |
| 50 | 7 | 10 | No precipitation |
| 10 | 7.5 | 40 | No precipitation |
| 20 | 7.5 | 40 | No precipitation |
| 40 | 7.5 | 40 | No precipitation |

As illustrated in Table 1, in the absence of $H_2O_2$, the solubility of EDTA in ethanol was very limited and resulted in precipitation of the solution. However, when $H_2O_2$ was present, even at very low concentrations, stable solutions of EDTA in ethanol were readily prepared with no precipitation being observed at either room temperature or after storage at 0° C.

Optionally, a viscosity-increasing agent, such as hydroxyl propyl methyl cellulose (HPMC), can be further added to the antimicrobial agents of the present application. Briefly, to prepare an antimicrobial agent comprising HPMC, two pre-mixes were initially prepared: Premix A and Premix B. In Premix A, which comprises 20.0 g of 3% USP $H_2O_2$ and 0.40 g disodium EDTA dehydrate, the ingredients were combined and mechanically mixed to complete dissolution. In Premix B, which comprises 0.27 g Dow K15M HPMC and 5.00 g absolute ethanol, the ingredients were combined and mixed well to make a smooth slurry. The Premix A solution was placed on a vigorous mechanical stirrer (magnetic) and treated with the slurry of Premix B from a disposable pipette. Care was taken to ensure that the pipette-filled slurry was representative of the whole, and to place the bolus from each pipette loading into the most active part of the vortex. The clear solution became cloudy immediately but did not clump or form visible separation. Addition of Premix B took approximately 5 minutes and then the whole mixture was stirred for an additional hour. At the end of that time, the solution became cloudy or somewhat opaque, but on standing for 15 minutes, the entrapped air had escaped and the solution became clear. Stirring was reinitiated and 15.0 g of absolute ethanol was slowly added to the mixture. The mixture was initially clear, but at approximately 31% ethanol content (e.g., when approximately 8.3 g of ethanol had been added), the mixture became increasingly cloudy. After ethanol addition was complete, the mixture was stirred for another 15 minutes. The resulting thickened mixture had a pearlescent appearance, and could be used after mild shaking or simple stirring.

The initial viscosity was approximately 330 cps (Brookfield LVF2 @ 30 rpm). The viscosity leveled off at about 270-280 cps after 10 days of standing at room temperature.

Example 2

Antimicrobial Activity of the Antimicrobial Agent

To illustrate the efficacy of the antimicrobial agents of the present application, three representative pathogenic microorganisms were chosen for the experiments. *Candida albicans* is a fungal species, methicillin resistant *Staphylococcus aureus* (MRSA) is a gram-positive bacterial species and *Pseudomonas aeruginosa* is a gram-negative bacterial species.

Each test microorganism was inoculated in Brain Heart Infusion broth (BHIB) and incubated at 37° C. for 20 h-36 h, yielding a culture containing minimally $10^8$ colony forming units per milliliter (CFU/mL). Determination of the initial CFU/mL of the culture was accomplished using dilution plating onto Brain-Heart Infusion agar (BHIA) followed by incubation at 37° C. for 24 h.

To test the efficacy of the antimicrobial agents of the present application, 1 mL of culture was pipetted into 5 mL of antimicrobial agent solution yielding a 5:1 ratio. This combination of the antimicrobial agent solution and microorganism was immediately vortexed and allowed to sit without disruption for the desired time interval. Once the desired time interval had been completed, the antimicrobial agent solution underwent filtration.

A syringe filtration device with a removable membrane functioned to catch any microorganisms, while the antimicrobial agent solution and broth were allowed to pass through, ensuring that the microorganism were in contact with the antimicrobial agent solution for the desired amount of time. Using a 0.2 m syringe, 1 mL of the mixture of microorganism culture and antimicrobial agent solution was passed through the filter. Approximately 2 mL of sterile 0.85% saline was used to rinse any residual antimicrobial agent solution from the filter. The membrane was then sterilely removed and subsequently placed onto a BHIA plate and incubated for 24 h to allow for CFU determination. The membrane allowed diffusion of the nutrients from the agar to any viable cells, resulting in formation of colonies. Any growth on the membrane was confirmed by removal of a single colony, streaked for isolation and gram stained. Additionally, in the absence of growth, a swab was taken from the membrane and subcultured on BHIA.

Table 2 summarizes the efficacy of the different antimicrobial agent solutions tested in killing *C. albicans*, MRSA and *P. aeruginoa*.

TABLE 2

| EtOH (% v/v) | $H_2O_2$ (% v/v) | EDTA (mg/mL) | C. albicans | MRSA | P.aeruginoa |
|---|---|---|---|---|---|
| 25 | 0.5 | 15 | Treatment time | Treatment time | Not tested |
| | | | 2 min—Lawn observed | 2 min—Lawn observed | |
| | | | 15 min—64 CFU | 15 min—Lawn observed | |
| | | | 1 hour—0 CFU | 1 hour—Lawn observed | |
| | | | 4 hours—0 CFU | | |
| | | | 6 hours—0 CFU | 4 hours—2 CFU | |
| | | | Initial culture 0.4-1 × $10^8$ CFU/mL | 6 hours—N/A | |
| | | | | Initial culture 7.8-10.3 × $10^7$ CFU/mL | |

TABLE 2-continued

| EtOH (% v/v) | $H_2O_2$ (% v/v) | EDTA (mg/mL) | C. albicans | MRSA | P.aeruginoa |
|---|---|---|---|---|---|
| 25 | 1 | 10 | Treatment time<br>2 min—Lawn observed<br>15 min—4 CFU<br>1 hour—0 CFU<br>4 hours—0 CFU<br>6 hours—0 CFU<br>Initial culture 0.4-1 × $10^8$ CFU/mL | Treatment time<br>2 min—Lawn observed<br>15 min—Lawn observed<br>1 hour—Lawn observed<br>4 hours—0 CFU<br>6 hours—0 CFU<br>Initial culture 7.8-10.3 × $10^7$ CFU/mL | Not tested |
| 50 | 1 | 10 | Treatment time<br>2 min—0 CFU<br>15 min—0 CFU<br>1 hour—0 CFU<br>4 hours—0 CFU<br>6 hours—0 CFU<br>Initial culture 0.4-1 × $10^8$ CFU/mL | Treatment time<br>2 min—0 CFU<br>15 min—0 CFU<br>1 hour—0 CFU<br>4 hours—0 CFU<br>6 hours—0 CFU<br>Initial culture 7.8-10.3 × $10^7$ CFU/mL | Not tested |
| 50 | 0.5 | 7.5 | Treatment time<br>2 min—0 CFU<br>15 min—0 CFU<br>1 hour—0 CFU<br>4 hours—0 CFU<br>6 hours—0 CFU<br>Initial culture 0.4-1 × $10^8$ CFU/mL<br>No growth observed in subcultured filter membranes | Treatment time<br>2 min—0 CFU<br>15 min—0 CFU<br>1 hour—0 CFU<br>4 hours—0 CFU<br>6 hours—0 CFU<br>Initial culture 0.2-7 × $10^8$ CFU/mL<br>No growth observed in subcultured filter membranes | Treatment time<br>2 min—0 CFU<br>15 min—0 CFU<br>1 hour—0 CFU<br>4 hours—0 CFU<br>6 hours—0 CFU<br>Initial culture 2.2-3.3 × $10^9$ CFU/mL |
| 50 | 6 | 40 | Treatment time<br>30 sec—0 CFU<br>60 sec—0 CFU<br>2 min—0 CFU<br>15 min—0 CFU<br>1 hour—0 CFU<br>Initial culture 1.8-2.2 × $10^8$ CFU/mL<br>No growth observed in subcultured filter membranes | Treatment time<br>30 sec—0 CFU<br>60 sec—0 CFU<br>2 min—0 CFU<br>15 min—0 CFU<br>1 hour—0 CFU<br>Initial culture 4.8-7 × $10^8$ CFU/mL<br>No growth observed in subcultured filter membranes | Treatment time<br>30 sec—0 CFU<br>60 sec—0 CFU<br>2 min—0 CFU<br>15 min—0 CFU<br>1 hour—0 CFU<br>Initial culture 2.8-3.3 × $10^9$ CFU/mL |
| 60 | 3 | 10 | Treatment time<br>30 sec—0 CFU<br>60 sec—0 CFU<br>2 min—0 CFU<br>15 min—0 CFU<br>1 hour—0 CFU<br>Initial culture 0.8-2.2 × $10^7$ CFU/mL<br>No growth observed in subcultured filter membranes | Treatment time<br>30 sec—1 CFU<br>60 sec—0 CFU<br>2 min—0 CFU<br>15 min—0 CFU<br>1 hour—0 CFU<br>Initial culture 4.8-7 × $10^8$ CFU/mL<br>No growth observed in subcultured filter membranes | Treatment time<br>30 sec—0 CFU<br>60 sec—0 CFU<br>2 min—0 CFU<br>15 min—0 CFU<br>1 hour—0 CFU<br>Initial culture 2.8-3.3 × $10^9$ CFU/mL |

As illustrated in Table 2, antimicrobial agent solutions comprising low concentrations of ethanol were not as effective in killing *C. albicans* and MRSA (*P. aeruginoa* killing was not tested). However, in the presence of higher concentrations of ethanol, there was a loss of viability of all three strains tested, as demonstrated by the lack of growth at all exposure/treatment times, even as early as 30 seconds.

The combination of components within the antimicrobial agents of the present application demonstrated lethality and were effective in killing three representative and deadly catheter-related blood stream infection (CRBSI) pathogens: *Candida albican*, MRSA, and *Pseudomonas aeruginosa*, in only 30 seconds, even with very high bacterial inocula. Thus, the antimicrobial agents of the present application were superior to other antimicrobial agents that offer only a limited spectrum of organisms, i.e., no bacterial or fungal spores, with treatment times of 10-15 minutes, and frequently with lower inocula tested.

Example 3

Immunomodulatory Activity of the Antimicrobial Agent

To test whether the inflammatory milieu present during an infection might activate or be associated with cancer (and pre-cancerous) development and/or progression, a human subject that had developed chronic periodontitis and displayed leukoplakia lesions within the oral cavity was studied.

The human subject was diagnosed with chronic periodontitis, an inflammatory condition characterized by chronic inflammation of the periodontal tissues that is caused by accumulation of profuse amounts of dental plaque. Chronic periodontitis may be initiated by Gram-negative and Gram-positive tooth and gingival-associated bacteria, usually anaerobic or microaerophilic organisms and biofilms that elicit a host response, which results in bone and soft tissue destruction. This disease is associated with a variable microbial pattern. In response to endotoxin derived from periodontal pathogens, several osteoclast-related mediators target the destruction of alveolar bone and supporting connective tissue such as the periodontal ligament. Some major drivers of this aggressive tissue destruction include matrix metalloproteinases (MMPs), cathepsins, and other osteoclast-derived enzymes.

In addition to the being diagnosed with chronic periodontitis, the subject developed leukoplakia lesions within the oral cavity displaying invasive squamous cell carcinoma with surrounding carcinoma-in-situ and dysplasia in the right mandibular gingival area. Visual inspection of the lesions appeared as white, translucent patches. Histological examination of biopsy specimens from the affected areas revealed evidence of surface epithelium exhibiting extensive atypia with underlying fibrous connective tissue. The epithelial cells showed evidence of loss of maturation, nuclear hyperchromatism and nuclear crowding. The underlying connective tissue showed infiltration by lymphocytes, plasma cells and neutrophils, characteristic of an inflammatory reaction. The epithelium also showed signs of verucous hyperparakeratosis and orthokeratosis, irregular acanthosis and basilar hyperplasia with mild epithelial hyperplasia, suggestive of a stage of proliferative verrucous leukoplakia, a form of squamous cell carcinoma. Previously, the subject's dentists had attempted to treat the chronic periodontitis and leukoplakia with a succession of oral antibiotics, antifungal fluconazole and prolonged courses of chlorhexidine oral rinses, in addition to vigorous dental hygiene. All of these therapeutic measures failed significantly to improve his condition or prevent progression to oral cancer.

A single topical application of the antimicrobial agent of the present application in solution form was applied to the right lower mandibular gingival area while the right upper mandibular gingival area remained untreated. Visual inspection of the antimicrobial agent-treated area produced noticeable reduction in both the size and severity of the lesion within approximately 10 hours. Continued daily or twice-daily applications of the antimicrobial agent solution to the right lower mandibular gingival area over 12 days were effective to further reduce the lesion to approximately 1 mm. Subsequent biopsy of the lesion and examination by histological examination revealed no evidence of invasive carcinoma, with only slight dysplasia being present. No signs of inflammatory cells were observed post treatment. In contrast, the pathology of the untreated right upper mandibular gingival area continued to display signs of invasive squamous cell carcinoma and was only finally removed by surgery post treatment.

These results suggest that the antimicrobial agent of the present application was effective as an immunomodulator in treating conditions such as invasive squamous cell carcinomas that may have developed as a result of the pre-existing inflammatory condition.

In addition to visual inspection of the treated area, the subject's upper and lower mandibular areas were examined pre- and post-treatment for the following physical characteristics: bleeding, suppuration, plaque, calculus, pocket depth and clinical attrition. Of the 32 teeth from the subject, 192 sites were examined for the physical characteristics as summarized in Table 3 below.

TABLE 3

|  | Teeth | Sites Examined | % (Pre-treatment) | % (Posi-treatment) | % Change |
|---|---|---|---|---|---|
| Total Teeth | 32 | 192 | — | — | — |
| Bleeding | 19/0 | 36/0 | 19 | 0 | 19% improvement |

TABLE 3-continued

|  | Teeth | Sites Examined | % (Pre-treatment) | % (Posi-treatment) | % Change |
|---|---|---|---|---|---|
| Suppuration | 0/0 | 0/0 | 0 | 0 | No change |
| Plaque | 0/0 | 0/0 | 0 | 0 | No change |
| Calculus | 0/0 | 0/0 | 0 | 0 | No change |
| 1-3 mm pocket depth | 25/13 | 114/50 | 59 | 26 | 33% improvement |
| 4-5 mm pocket depth | 13/12 | 30/41 | 16 | 21 | 5% worsening |
| 6+ mm pocket depth | 4/4 | 6/5 | 3 | 3 | No change |
| 1-3 mm clinical attrition | 10/6 | 19/20 | 10 | 10 | No change |
| 4-5 mm clinical attrition | 21/13 | 66/27 | 34 | 14 | 20% improvement |
| 6+ mm clinical attrition | 22/12 | 65/49 | 34 | 26 | 8% improvement |

Based on the clinical measurements, treatment with the antimicrobial agent of the present application improved many physical characteristics of the subject including bleeding (by 19%), 1-3 mm pocket depth (by 33%), 4-5 mm clinical attrition (by 20%) and 6+mm clinical attrition (by 8%). There were no changes to the subject's 6+mm pocket depth and 1-3 mm clinical attrition and about a 5% worsening of the subject's 4-5 mm pocket depth. These clinical results further suggest that the antimicrobial agent of the present application was effective in improving the overall oral health of the subject, which may be due to its role as a potent immunomodulator.

In order to confirm that the effect of the antimicrobial agent solution was immunomodulatory and not anti-viral, biopsy samples from the same human subject were examined for the presence of human papilloma virus (HPV). A complete screen, testing for 37 different HPV species was negative, including HPV-16 and 18, the most common causes of genital cancers. Specifically, using a PCR amplified protocol in conjunction with a Luminex bead assay detection system, the following HPV species were tested: HPV 6, 11, 16, 18, 26, 31, 33, 35, 39, 40, 42, 45, 51, 52, 53, 54, 55, 56, 58, 59, 61, 62, 64, 66, 67, 68, 69, 70, 71, 72, 73, 81, 82, 83, 84, IS39 and CP6108. No HPV species were detected in the biopsy samples although human DNA was detected.

These results provide further evidence that the cancer was unlikely to have been caused by viral infection of the most common type, although it does not rule out other viral causes.

Example 4

Anti-Viral Activity of the Antimicrobial Agent

The anti-viral activity of the antimicrobial agent of the present application was also studied in two human subjects that had developed cold sores.

Two human subjects had developed cold sores, which were consistent with a clinical diagnosis of recurrent herpes simplex virus (HSV) on the lips.

In the first subject, topical applications of the antimicrobial agent of the present application in solution form was applied to the cold sore affected area when the outbreak was producing an unbroken, fluid-filled, blister-like vesicle. Over the course of two days, significant shrinking and reduction of the vesicle to very small size was observed. The vesicle produced a small area of cracked skin that also healed rapidly with no visible lingering effects.

In the second subject, topical applications of the antimicrobial agent of the present application in solution form was applied to the cold sore affected area only after the vesicle had ruptured. The treated subject exhibited reduced severity and much more rapid healing than would be typical for cold sores in that subject.

The first subject had another recurring episode of a blister arising from a potential herpes simplex breakout on the lips and upon topical application of the antimicrobial agent of the present application in solution form, significant reduction and shrinking of the vesicle was observed. Continued topical application of the antimicrobial agent of the present application resulted in continued shrinking and reduction of the vesicle and rapid healing with no visible scabbing of the skin area.

Since herpes simplex is a virus, this data provides evidence that the antimicrobial agent of the present application exhibited anti-viral activity.

All references, including publications, patent applications and patents, cited herein are hereby incorporated by reference to the same extent as if each reference was individually and specifically indicated to be incorporated by reference and was set forth in its entirety herein.

Any combination of the above-described elements in all possible variations thereof is encompassed by the application unless otherwise indicated herein or otherwise clearly contradicted by context.

The terms "a" and "an" and "the" and similar referents as used in the context of describing the application are to be construed to cover both the singular and the plural, unless otherwise indicated herein or clearly contradicted by context.

The use of any and all examples, or exemplary language (e.g., "such as") provided herein, is intended merely to better illuminate the application and does not pose a limitation on the scope of the application unless otherwise indicated. No language in the specification should be construed as indicating any element is essential to the practice of the application unless as much is explicitly stated.

The description herein of any aspect or embodiment of the application using terms such as "comprising," "having," "including" or "containing" with reference to an element or elements is intended to provide support for a similar aspect or embodiment of the application that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). That said, the terms "comprising," "having," "including" or "containing" in the claims should be construed according to the conventional "open" meaning of those terms in the patent law to include those elements enumerated as well as other elements. Likewise, the terms "consisting of," "consists of," "consists essentially of," or "substantially comprises" should be construed according to the "closed" or "partially closed" meanings ascribed to those terms in the patent law.

This application includes all modifications and equivalents of the subject matter recited in the aspects or embodiments presented herein to the maximum extent permitted by applicable law.

We claim:

1. A method of treating, inhibiting or reducing a condition or disease, comprising administering to a subject a therapeutically effective amount of an antimicrobial solution comprising:

water;

from about 20% to about 60% by volume of ethanol;

from about 0.5% to about 7.5% by volume of a peroxide or peroxide-generating agent; and from about 5 mg/mL to about 40 mg/mL of a chelating agent wherein the chelating agent includes ethylenediamine tetraacetic acid (EDTA), acids of EDTA, salts of EDTA, or any combination thereof.

2. The method of claim 1, wherein the condition or disease is a bacterial condition or disease, a viral condition or disease, an inflammatory condition or disease, or immune response condition or disease.

3. The method of claim 1, wherein the solution is administered by topical application, intravenous injection, intraperitoneal injection or implantation, intramuscular injection or implantation, intralesional injection, subcutaneous injection or implantation, intradermal injection, suppositories, pessaries, enteric application, or nasal route.

4. The method of claim 1, wherein the solution is administered to a site selected from the group consisting of a wound site, a catheter site, a surgical site, an injection site, a catheter, a catheter lumen, a thermal burn site, a chemical burn site, a radiation burn site, a skin lesion, oral sites, bony sites, anal sites, vaginal sites, cervical sites, vulvar sites, penile sites, ulcerated skin sites, acne sites, actinic keratosis sites, inflamed sites, irritated sites, gastric sites, gastrointestinal sites, esophageal sites, esophagogastrointestinal sites, intestinal sites, cardiac sites, vascular sites, nasal sites, nasopharyngeal sites, and aural sites.

5. The method according to claim 1, wherein the low molecular weight alcohol is present at a concentration of about 50% by volume.

6. The method of claim 1, wherein the peroxide or peroxide-generating agent is present at a concentration of about 1.5% by volume.

7. The method according to claim 1, wherein the chelating agent is present at a concentration of about 10 mg/ml.

8. The method according to claim 1, wherein the peroxide or peroxide-generating agent comprises hydrogen peroxide.

9. The method according to claim 1, further comprising a viscosity increasing agent.

10. The method according to claim 9, wherein said viscosity increasing agent is carboxymethyl cellulose (CMC), hydroxypropyl methylcellulose (HPMC), methyl cellulose, methyl hydroxyethyl cellulose (MHEC), hydroxyethyl cellulose, sodium hydroxyalkyl celluloses, or admixtures thereof.

11. A method of treating, inhibiting or reducing a condition or disease, comprising administering to a subject a therapeutically effective amount of an antimicrobial solution consisting essentially of:

water;

from about 20% to about 60% by volume of ethanol;

from about 0.5% to about 7.5% by volume of a peroxide or peroxide-generating agent; and from about 5 mg/mL to about 40 mg/mL of a chelating agent wherein the chelating agent includes ethylenediamine tetraacetic acid (EDTA), acids of EDTA, salts of EDTA, or any combination thereof.

12. The method according to claim 11, wherein the peroxide or peroxide-generating agent comprises hydrogen peroxide.

* * * * *